United States Patent
Hu

(10) Patent No.: US 6,811,974 B2
(45) Date of Patent: Nov. 2, 2004

(54) PRIMER-SPECIFIC AND MISPAIR EXTENSION ASSAY FOR IDENTIFYING GENE VARIATION

(75) Inventor: Yu-Wen Hu, Gloucester (CA)

(73) Assignee: Canadian Blood Services, Ottawa (CA)

( * ) Notice: Subject to any disclaimer, the term of this patent is extended or adjusted under 35 U.S.C. 154(b) by 0 days.

(21) Appl. No.: 09/782,361

(22) Filed: Feb. 13, 2001

(65) Prior Publication Data

US 2002/0064778 A1 May 30, 2002

Related U.S. Application Data

(63) Continuation of application No. PCT/CA99/00733, filed on Aug. 9, 1999.

(30) Foreign Application Priority Data

Aug. 13, 1998 (CA) .............................................. 2245039

(51) Int. Cl.[7] ............................ C12Q 1/68; C12Q 1/70; C12P 19/34
(52) U.S. Cl. ............................... 435/6; 435/5; 435/91.2
(58) Field of Search ................................ 435/5, 6, 91.2

(56) References Cited

U.S. PATENT DOCUMENTS 5,527,669 A * 6/1996 Resnick et al. ................. 435/5
5,550,016 A * 8/1996 Okamoto ........................ 435/5

FOREIGN PATENT DOCUMENTS

WO WO 91/13075 9/1991
WO WO 94/01447 1/1994
WO WO 96/30545 10/1996

OTHER PUBLICATIONS

Lundberg, K. S. et al., "High–fidelity amplification using a thermostable DNA polymerase isolated from *Pyrococcus furiosus*", Gene, vol. 108, pp. 1–6 (1991).*
Hu, Y–W. et al., "Primer specific and mispair extension analysis (PSMEA) as a simple approach to fast genotyping", Nucl. Acids Res. vol. 26, pp. 5013–5015, Nov. 1, 1998.*
PCT International Preliminary Examination Report, PCT/CA99/00733 dated Oct. 30, 2000, 12 pages.
PCT International Search Report, PCT/CA99/00733 dated Jan. 13, 2000, 2 pages.

* cited by examiner

Primary Examiner—Jeffrey Fredman
Assistant Examiner—Teresa Strzelecka
(74) Attorney, Agent, or Firm—TraskBritt

(57) ABSTRACT

The invention relates to primer-specific and mispair extension assays for identifying gene variations, such as in different genotypes or subtypes of a given genotype. The assay includes extending a nucleic acid sequence from a patient sample with extension products of the primer, characterizing the extension products, and comparing the extension products with known nucleic acid sequences of various genotypes for determining the genotype of the nucleic acid sequence extended. In the assay, at least one primer or the dNTPs is labeled.

18 Claims, 10 Drawing Sheets

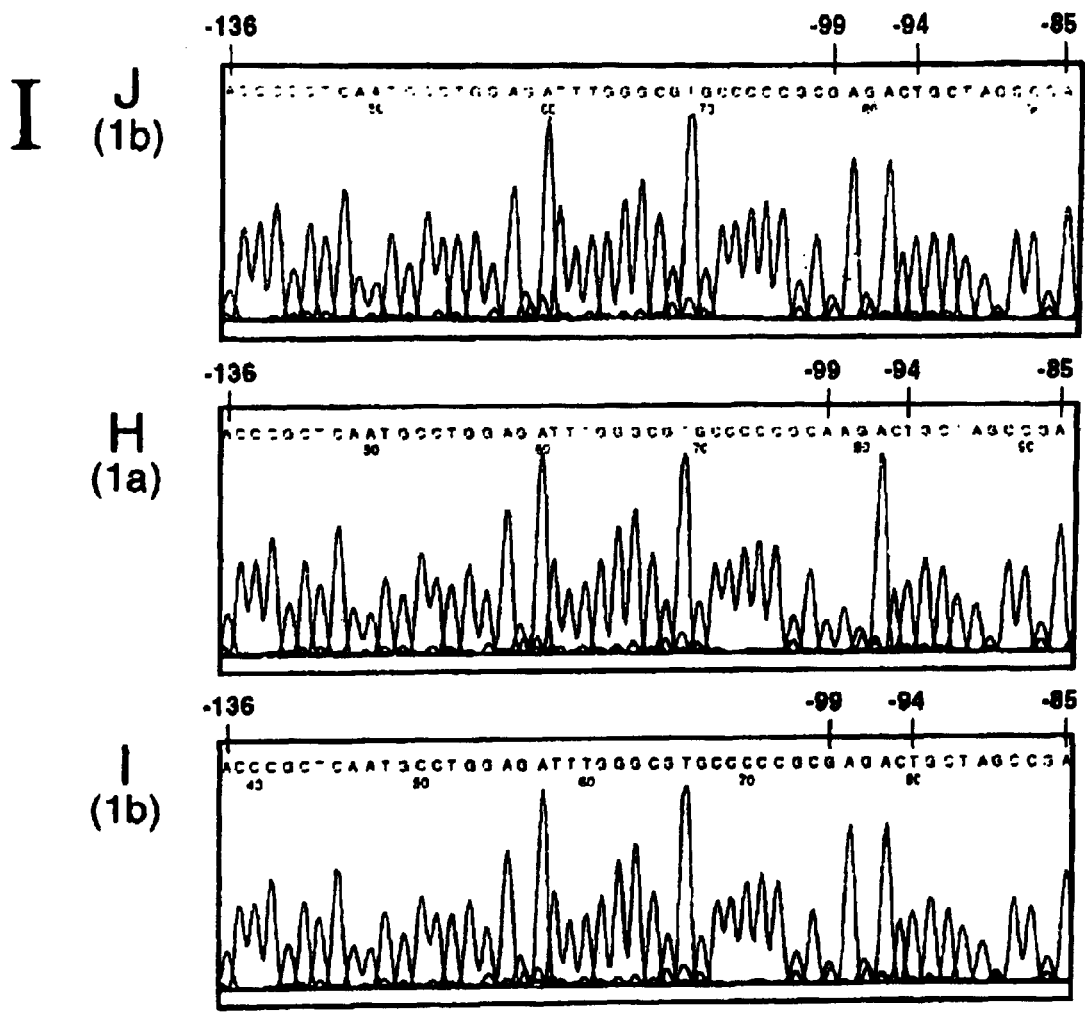
FIG. 4

| dNTPs | | Expected base extension |
|---|---|---|
| ATC | Primer →T CAXX | 3 |
| ATG | Primer →T X-XX | 1 |
| ACG | Primer →X-X | 0 |
| TCG | Primer →T CX--X | 2 |
| WT  ------A GTCCACATCCT---- (SEQ ID NO:16) | | |
| ATC | Primer →X  X | 0 |
| ATG | Primer →G  XX | 1 |
| ACG | Primer →G  CAGGX-X | 5 |
| TCG | Primer →G  CX--X | 2 |
| MU  ------C GTCCACATCCT---- (SEQ ID NO:17) | | |

```
3'  XTCATACTAXTCCATGAGTATCTTTAGACACCTGTATTTCG 5'  L63 + PRIMER    (1)  (SEQ ID NO:18)
5'  AGACAGTATGATCAGGTACTCATAGAAATCTGTGGACATAAAGC 3'  PRO63L(G)-R  (SEQ ID NO:19)
                    x

3'         GAGTATCTTTAGACACCTGTATTTCG 5'  L63P + PRIMER   (2)  (SEQ ID NO:20)
5'  AGACAGTATGATCAGGTACCCATAGAAATCTGTGGACATAAAGC 3'  PRO63L(G)-R  (SEQ ID NO:21)

3'  XTCATACTAXTCCATGGGTATCTTTAGACACCTGTATTTCG 5'  L63P + PRIMER   (3)  (SEQ ID NO:22)
5'  AGACAGTATGATCAGGTACCCATAGAAATCTGTGGACATAAAGC 3'  PRO63P(G)-R  (SEQ ID NO:21)
                    x

3'         GGGTATCTTTAGACACCTGTATTTCG 5'  L63 + PRIMER    (4)  (SEQ ID NO:23)
5'  AGACAGTATGATCAGGTACTCATAGAAATCTGTGGACATAAAGC 3'  PRO63P(G)-R  (SEQ ID NO:19)
```

FIG. 6A

```
3'       XXAGACTTCTGAGTCTAACCAACGTGAAATTTA 5' PRO90L-R   (1)  (SEQ ID NO:24)
5' ---AATCTGAAGACTCAGATTGGTTGCACTTTAAAT---3'       L90       (SEQ ID NO:25)
                  X

3'             TTCTGAGTCTAACCAACGTGAAATTTA 5' PRO90L-R   (2)  (SEQ ID NO:26)
5' ---AATCTGATGACTCAGATTGGTTGCACTTTAAAT---3'       L90M      (SEQ ID NO:27)

5' CTGTCAACATAATTGGAAGAAATCTGATGACGCCAGAXX 3' PRO90M-F   (3)  (SEQ ID NO:28)
3' ---GACAGTTGTATTAACCTTCTTTAGACTACTGCGGTCTAA---5'L90M         (SEQ ID NO:29)
                                          X

5' CTGTCAACATAATTGGAAGAAATCTGAT           3' PRO90M-F   (4)  (SEQ ID NO:30)
3' ---GACAGTTGTATTAACCTTCTTTAGACAACTGAGTCTAA---5'L90     (SEQ ID NO:31)
```

FIG. 7A

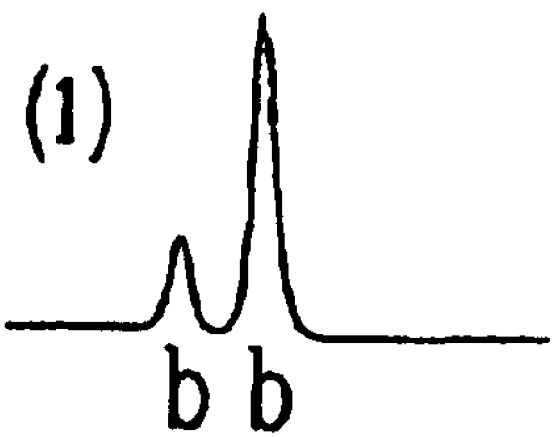
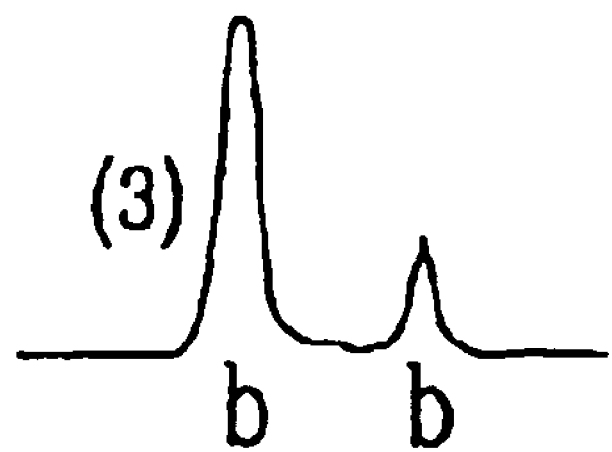
FIG. 7B

PRIMER-SPECIFIC AND MISPAIR EXTENSION ASSAY FOR IDENTIFYING GENE VARIATION

CROSS-REFERENCE TO RELATED APPLICATIONS

This application claims priority to, and is a continuation of, International Application No. PCT/CA99/00733, filed on Aug. 9, 1999, designating the United States of America, the contents of which are incorporated by this reference, the PCT International Patent Application itself claiming priority from the Canadian Application Serial No. 2,245,039 filed Aug. 13, 1998.

BACKGROUND OF THE INVENTION

1. Field of the Invention

The invention relates to primer-specific and mispair extension assay for identifying gene variations, such as in different genotypes or subtypes of a given genotype.

2. State of the Art

Current genotyping systems are technically complex, time-consuming and error-prone in the detection of a single nucleotide variation and low level heterozygotes.

Despite current genotyping systems, such as restriction fragment length polymorphism analysis (RFLP), hybridization for example, line probe assay ("LiPA"), selective DNA amplification by PCR-type-specific primers (Okamoto, H., et al., *J. Gen. Virol.* 73: 673, 678, 1992) and direct DNA sequencing having been useful in general, some technical problems still remain and limit their applications.

Development of viral resistance to antiviral drugs used for treatment of HIV-1 infection is an important cause of treatment failure (Coffin J M., *Sciences,* 267: 483–489, 1995). In addition, drug-resistant mutations can give rise to selective cross-resistance to other antiviral drugs which has limited the options available for alternative antiviral regimens (Cohen O J, and Fauci A S., *N. Engl. J. Med.,* 339: 341–243, 1998). Thus, genotypic drug resistance testing plays an important role in selecting an initial antiviral regimen and changing therapy with alternate regimens as the need arises. However, current genotyping assays, including direct DNA sequencing, yield information on only the predominant viral quasispecies due to the inability of these assays to detect low levels of viral variants (Günthard, H. F., et al., *AIDS Res. Hum. Retroviruses,* 14: 869–876, 1998). An ABI automated sequencer was able to detect mutants at levels of 10–50% in an artificially mixed sample only when the mixes were analyzed by editing the sequences manually. Hybridization-based high-density oligonucleotide arrays (GeneChip) (Deeks S G, Abrams D I., *Lancet,* 349: 1489–1490, 1997) were less sensitive than the ABI and were able to detect mutations at levels of 25–75% in the mix (Günthard, H. F., et al, *AIDS Res. Hum. Retroviruses,* 14: 869–876, 1998). Similar results were obtained using an automated DNA sequencer (Visible Genetics) (Hu Y W, et al., Reliable detection of mixed HCV genotype infections using a novel genotyping assay. 5$^{th}$ International Meeting on Viral Hepatitis C Virus and Related Viruses, Molecular Virology and Pathogenesis, Venezia, Italy, 1998). Line Probe Assay ("LiPA"), which uses reverse hybridization technology, is relatively rapid and could detect mutants at levels as low as 5% (Stuyver L, et al., *Antimicrob. Agents Chemother.,* 41: 284–291, 1997), but again, may not be suitable for detection of mixed genotypes because it may not give results due to nearby polymorphisms that impair hybridization (Stuyver L, et al., *Antimicrob. Agents Chemother.,* 41: 284–291, 1997). Moreover, in 40% of the samples tested, LiPA failed to yield correct results for some of the drug-resistant mutations (Puchhammer-Stockl E, et al, *J. Med. Virol.,* 57: 283–289, 1999). Population based sequencing, for example, cloning and sequencing, is the gold standard method for detection of minor drug-resistant mutants. Unfortunately, it is impractical for clinics and large cohort studies.

For most indirect DNA sequencing genotyping systems, a common weakness is that they are not as accurate as direct DNA sequencing analysis, particularly for detection of a single nucleotide mutation or variation, resulting in considerable instances of errors or inconsistent results (Andonov, A., et al., *J. Clin. Microbiol.* 32: 2031–2034, 1994; Tuveri, R., et al., *Journal of Medical Virology* 51: 36–41, 1997; Okamoto, H., et al., *J. Virol. Methods* 57: 31 45 002–16, 1996). Although direct DNA sequencing is the most reliable method for genotyping, this is not practical for large cohort studies.

For example, International Publication No. WO 91/13075 describes a method for detecting variable nucleotides based on primer extension and incorporation of detectable nucleoside triphosphate using T7 polymerase for extending the primer. However, T7 polymerase does not have the proofreading activity and the 3'-5' exonuclease activity of pfu results in false positive or false negative reactions. Moreover, the method uses ddNTPs for terminating extension.

Another major limitation of all current genotyping systems, including direct DNA sequencing, is that they cannot reliably detect low levels of heterozygotes (Tuveri, R., et al, *Journal of Medical Virology* 51: 36–41, 1997; Lau, J. Y., et al., *J. Infect. Dis.* 171: 281–289, 1995; Forns, X., et al., *J. Clin. Microbiology.* 34–10: 2516–2521, 1996) or mixed genotype infections (Tuveri, R., et al., *Journal of Medical Virology* 51: 36–41, 1997; Lau, J. Y., et al., *J. Infect. Dis.* 171: 281–289, 1995; Forns, X., et al., *J. Clin. Microbiology.* 34–10: 2516–2521, 1996).

International Publication No. WO 96/30545 discloses a method for simultaneously analyzing a genetic mutation and a corresponding wild-type sequence within a sample. The method utilizes ddNTPs for terminating primer extension. However, the use of ddNTPs increases the background of the assay, reducing its sensitivity and capacity to detect low levels of heterozygotes, similarly as in WO 91/13075.

HCV was recognized as the major etiologic agent of blood borne non-A, non-B hepatitis soon after the virus was identified in 1989. As an RNA virus, HCV shows great genetic variability, resulting in the existence of types, subtypes and quasispecies. At present, 11 types and at least 50 subtypes have been described. However, types 1a, 1b, 2a, 2b and 3a have been found to be generally the most prevalent (Simmonds, P., *Hepatology* 21: 570–582, 1995). Subtype 1b is the most common genotype found in Japan (Okamoto, H., et al., *J. Gen. Virol* 73: 673, 678, 1992) and European countries while subtypes 1a and 1b are the most common genotypes in the United States (Lau, J. Y., et al., *J. Infect. Dis.* 171: 281–289, 1995) and Canada, (Andonov, A., et al., *J. Clin. Microbiol.* 32: 2031–2034, 1994). Viruses of various genotypes contain different antigenic properties, which have potentially important consequences for the development of a vaccine and for antibody screening tests. Also, the disease severity and response to interferon may be influenced by the virus types and subtypes (Simmonds, *Hepatology* 21: 570–582, 1995). Subtype 1b was reported to be associated with a high severity of the disease and low response to interferon (Simmonds, *Hepatology* 21: 570–582, 1995). It is apparent that a rapid, simple, accurate and inexpensive genotyping method is urgently needed.

Amplification refractory mutation system ("ARMS") (Newton, C. R., et al., *Nucl. Acids Res.* 17: 2503–2516), improved the methods used in the prior art for typing the five most common genotypes (Pistello, M., et al., *J. Clin. Microbiol.* 32: 232–234, 1994). ARMS was developed for PCR detection of any point mutation in DNA using Taq DNA polymerase (Newton, C. R., et al., *Nucl. Acids Res.* 17: 2503–2516) and is based on the principle that oligonucleotides with a mismatched 3'-residue would not function as primers in PCR under controlled conditions. In some cases, however, the specificity of ARMS was insufficient to give a correct diagnosis. The problem with nonspecific reactivities still remains with the type-specific primer PCR method for HCV genotyping, even with the improvement using ARMS.

It is apparent that the major cause of the nonspecific reactivities found in these assays is related to the use of Taq DNA polymerase due to its lack of 3'→5' exonuclease activity. This inaccuracy results in base substitutions, transitions, tranversions, frame shifts or deletion mutations during DNA synthesis. Consequently, mispairs can be frequently formed, and Taq polymerase would be able to continue synthesizing DNA by addition of the next correct nucleotide on the template (Lau, J. Y., et al., *J. Infect Dis.* 171: 281–289, 1995). Even after reaching the end of the template, several more nucleotides can be added to the extended primer because most DNA polymerases, including Taq and retroviral reverse transcriptase (RT), have a nontemplate-dependent DNA synthesis activity, for example, terminal deoxynucleotide transferase activity (Clark, J. M., *Nucleic Acids Res.* 16: 9677; and Patel, P. H., et al., *Proc. Natl. Acad. Sci. U.S.A.* 91: 549–553). Therefore, the nonspecific reaction cannot be avoided with either ARMS or the methods based on ARMS using Taq DNA polymerase.

Two thermostable DNA, polymerases pfu (*Pyrococcus furiosus*) (Lundberg, K. S., et al., *Pyrococcus furiousus. Gene* 108: 1–6, 1991), and TLI/Vent (*Thermococcus litoralis*), (Neuner, A., et al., *Iarch. Microbiol.,* 153: 205–207), exhibit 3'→5' proofreading exonuclease activity. This ensures a high degree of amplification fidelity during DNA polymerization. Unlike Vent, the pfu 3'→5' exonuclease activity peaks sharply at its optimal polymerization temperature (75° C. to 80° C.), minimizing undesirable primer-degradation activity (Lundberg, K. S., et al., *Gene* 108: 1–6, 1991). Pfu DNA polymerase also does not exhibit terminal deoxynucleotidyl-transferase (TDT) activity, which was reported to be involved in the high mutation rate of DNA during DNA polymerization.

It would be highly desirable to be provided with a simple assay or method to overcome many of these limitations of current DNA genotyping systems.

It would be highly desirable to be provided with genotypic assays that possess greater accuracy and sensitivity for detection of minor drug-resistant subpopulations of HIV-1 in the early stages of resistance evolution.

DISCLOSURE OF THE INVENTION

One aim of the present invention is to provide a novel primer-specific and mispair extension assay (PSMEA) for determining genotypes and subtypes.

Another aim of the present invention is to provide a primer-specific and mispair extension assay (PSMEA) for detecting nucleotide variations in any known gene sequence using pfu DNA polymerase in the presence of an incomplete set of dNTPs and only a single primer.

Another aim of the present invention is to provide a tool for reliable detection of mixed genotype infection.

Another aim of the present invention is to provide a sensitive tool for detecting low levels of drug-resistant mutants in patients being treated with antiviral drugs.

Another aim of the present invention is to provide a tool for accurate genotyping.

In accordance with the present invention, there is provided a primer-specific and mispair extension assay for determining genotype. The assay includes:

a) extending a nucleic acid sequence from a patient sample with a polymerase, more preferably a pfu DNA polymerase, using a primer-specific for a genotype to be determined and an incomplete set of dNTPs, under suitable conditions for obtaining extension products of the primer, wherein at least one of the primer or the dNTPs is labeled;

b) characterizing the extension products; and c) comparing the extension products with known nucleic acid sequences of various genotypes for determining the genotype of the nucleic acid sequence extended.

Preferably, characterizing the extension products includes separating the extension products by size. More preferably, characterizing the extension products further includes sequencing the extension products after separating the extension products by size.

Alternatively, the assay may further include amplifying the nucleic acid sequence before extending the nucleic acid sequence from a patient sample.

Preferably, the incomplete set of dNTPs contains two or three different types of nucleotides.

In a preferred embodiment, the primer is labeled with a radioactive label or a fluorescent label.

In another embodiment, one of the dNTPs is labeled with a radioactive label or a fluorescent label.

In accordance with the present invention, there is provided a novel genotyping system, primer-specific and mispair extension analysis (PSMEA) preferably using the unique 3' to 5' exonuclease proofreading properties of pfu DNA polymerase with an incomplete set of dNTPs and only a single primer.

Also in accordance with one embodiment of the present invention there is provided a primer-specific and mispair extension assay for determining genotype and detecting low level mixed genotype injections or heterozygotes. The assay includes:

a) extending a DNA sequence, amplified from a patient sample, with pfu DNA polymerase using a primer-specific for a genotype to be determined and an incomplete set of dNTPs, under suitable conditions for extending the primer, wherein at least one of the primer or one of the dNTPs is labeled;

b) separating the extended DNA sequences obtained in step a);

c) detecting the separated extended DNA sequences; and d) comparing the extended DNA sequences with known DNA sequences of various genotypes for determining the genotype of the DNA sequences extended.

The primer may be end-labeled with a label or one of the dNTPs can be labeled with a label. The label can be a radioactive or fluorescent label.

Preferably, the steps a), b), c), and d) as described above are automated.

BRIEF DESCRIPTION OF THE SEVERAL VIEWS OF THE DRAWINGS

FIG. 2 illustrates nucleotide deletions and insertions by PSMEA with primer 6AR-1 and 6AR-2 extensions by pfu on templates 1a and 6a;

FIG. 4 illustrates a typical profile of unlabeled primer extensions by pfu on HCV templates for types 1a, 1b, 2a, 2b, 3a and 3b using $^{32}$P-labeled dCTP and dGTP;

FIGS. 6A and 6B illustrate the detection of HIV-1 drug-resistant mutant L63P and wild type L63 using matched and mismatched pairs at the 3' end of the primers in PSMEA;

FIGS. 7A and 73B illustrate the detection of HIV-1 drug-resistant L90M and wild type L90 using matched and mismatched pairs at the 3' end of the primers.

DETAILED DESCRIPTION OF THE INVENTION

Figure 1:
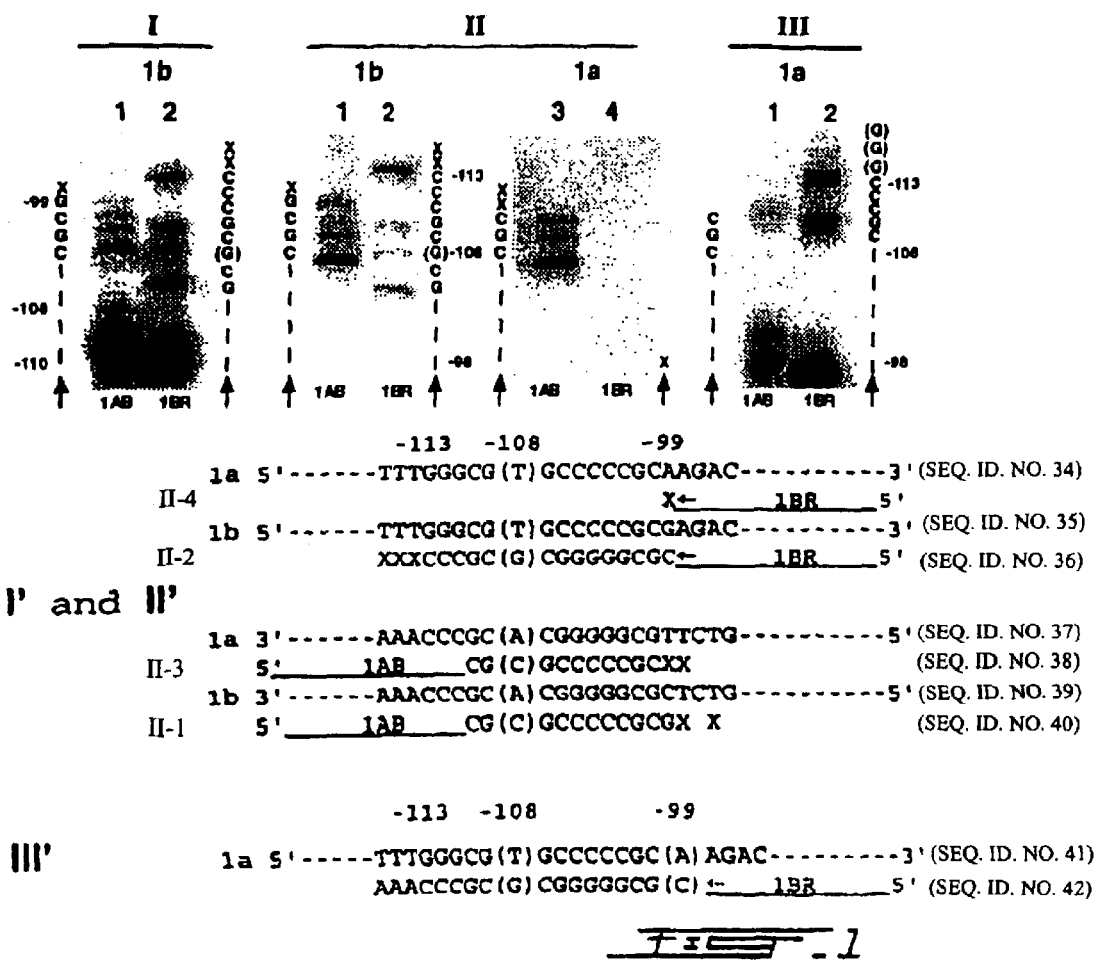
FIG. 1 illustrates characteristics of primer-specific and mispair extension by pfu and Taq DNA polymerase.

In accordance with one embodiment of the invention, a novel primer-specific and mispair extension assay (PSMEA) is provided for determining genotypes and more preferably, Hepatitis C virus (HCV) genotypes and subtypes.

PSMEA is used to detect nucleotide variations in any known gene sequence using pfu DNA polymerase in the presence of an incomplete set of dNTPs. To test the feasibility of PSMEA, the 5' untranslated region ("UR") of the HCV genome, known for being highly conservative, was used as a model for analysis of the nucleotide variation in determining the type and subtype of the virus. The results demonstrate that PSMEA is a rapid, simple and accurate method for HCV genotyping.

In the 5' UR of the HCV genome, six major genotypes and some subtypes can be classified by the nucleotide variation in this region (Simmonds, P., *Hepatology* 21: 570–582, 1995; Stuyver, L., et al., *J. Clin. Microbiol.* 34; 2259–2266, 1996).

The PSMEA of the present invention is a simple method with great potential for accurately detecting nucleotide mutations and which may be used for detecting nucleotide variations in any known gene sequence.

PSMEA is based on the unique properties of 3'→5' proofreading activity in a reaction with an incomplete set of dNTPs. Under such reaction conditions in accordance with one embodiment of the invention, pfu is extremely discriminating in nucleotide incorporation and proofreading at the initiation step of DNA synthesis, allowing for an accurate detection of nucleotide variation and heterozygotes in PSMEA.

It is known that under this reaction condition mispair formation and extension occur during DNA synthesis when using reverse transcriptase and DNA polymerases, including enzymes that exhibit 3'→5' proofreading exonuclease activity (Perinno, F., et al., *Proc. Natl. Acad. Sci. USA.* 86: 8343–8347, 1989; Reha-Krantz, L. J., et al., *Proc. Natl. Acad. Sci. USA.* 88: 2417–2421, 1991). However, the frequency of mispair formation and extension depends on whether the polymerase possesses 3'→5' exonuclease activity, the concentration of nucleotide substrates and the composition of the mispairs (Reha-Krantz, et al., *Proc. Natl. Acad. Sci. USA.* 88: 2417–2421, 1991). Accordingly, the characteristics of primer-specific and mispair extension by thermostable DNA polymerases including pfu (*Pyrococcus furiosus*) (Lundberg, K. S., et al., *Gene* 108: 1–6, 1991), Taq (*Thermus aquaticus*) (Saiki, R. K., et al., *Science.* 239: 487, 1988), and TLI/Vent (*Thermococcus litoralis*) (Neuner, A., et al., *Iarch. Microbiol.*, 153: 205–207) were further investigated. Several characteristics of primer-specific and mispair extension by pfu were observed and found to be useful for reliable detection of nucleotide variation, deletion and insertion, as well as heterozygotes.

In accordance with a preferred embodiment of the invention, the accuracy was evaluated by assaying the nucleotide variations between genotypes in the 5' untranslated region (5' UR) of the hepatitis C virus (HCV) genome. Mixed infections with more than one genotype of HCV were used for comparison of the sensitivity of PSMEA with other assays in the detection of heterozygotes. The feasibility of the method of the present invention for large cohort studies was demonstrated by genotyping a total of two hundred and forty-five (245) HCV isolates. The results show that PSMEA is an extraordinarily accurate system for identifying nucleotide variation, genotyping and detecting heterozygous molecules, and is readily applicable for routine use.

The design of PSMEA in accordance with a preferred embodiment of the invention is based on a single primer extension by the pfu DNA polymerase in the presence of only dCTP and dGTP, permitting accurate detection of nucleotide variations in the 5' untranslated region (5'UR) of the HCV genome. In accordance with one embodiment of the invention, the HCV genotypes from ninety-six (96) patients and blood donors with HCV infection were determined by PSMEA. Seventy-four (74) of the samples were also genotyped by either the line probe assay ("LiPA") or restriction fragment length polymorphism ("RFLP") methods. Genotypes were confirmed by nucleotide sequencing as required. HCV Isolates, including types and subtypes 1a, 1b, 2a, 2b, 2c, 3a, 3b, 4a, 5a, and 6a, were clearly identified by the PSMEA of the present invention. All of the types and subtypes determined by PSMEA were matched with those identified by LiPA or RFLP. Five (5) isolates of subtypes 1a and 1b that could not be typed by LiPA were clearly identified by the PSMEA of the present invention.

The primers used in the present invention were designed to meet the following requirements: 1) the sequence of primer binding site on template should be a type- or subtype-specific; 2) primers used for PSMEA should exhibit a similar melting temperature. In accordance with the present invention, 11 primers were designed for HCV genotyping with PSMEA (Table 1).

FIG. 1 illustrates preferred characteristics of primer-specific and mispair extension by pfu.

FIG. 1, column I illustrates $^{32}$P-labeled primer extensions by pfu on template HCV genotype 1b in the presence of dCTP and dGTP (FIG. 1, columns I-1 and I-2) used as markers for the length of primers and extended products. Column II illustrates the use of $^{32}$P-labeled dNTPs instead of labeled primers for PSMEA under the same reaction conditions, showing the difference in primer extension between HCV genotypes 1a and 1b (FIG. 1, columns II-1, II-2, II-3 and II-4). Column III illustrates mispair formation and extension by Taq on template 1a with $^{32}$P-labeled primers 1AB and 1BR (FIG. 1, columns III-1 and III-2). FIG. 1, parts I', II' and III' illustrate the nucleotide sequences extended on templates of HCV genotypes 1a and 1b. Primer 1AB extended on the antisense strand of templates 1a and 1b. X, XX and XXX represent the sites of nucleotide mismatches that terminated primer extension. →represents a nucleotide at the 3' end of the primer that is complementary to the opposite nucleotide in the template. (A), (C), (G) or (T) denotes the position of the nucleotide when a mispair is produced. −113, −108 and −99 are the nucleotide positions in 5'UR of HCV. The underlined sequence indicates the primer binding sites. The signs in this figure are used for all other figures.

A mismatched pair with nucleotide A at position −99 of the template HCV genotype 1a that is opposite the first nucleotide to be incorporated at the 3' end of primer, could not be produced and subsequently, aborted the primer extension by pfu in the presence of dCTP and dGTP (FIG. 1, column I-1). Under the same reaction conditions, the primer extended on the template of genotype 1b because nucleotide A becomes G at position −99 (FIG. 1, column I-2), differentiating between genotypes 1a and 1b with this single nucleotide variation that is the only difference in the 5' UR between the two genotypes.

FIG. 1 illustrates the alignment of the 5' UR nucleotide sequences of HCV subtypes 1a and 1b, showing the homologous sequence( - - - ) and the difference of the nucleotide at position −99 (A for 1a and G for 1b). The primer extension stopped at position −99 where a mismatched pair(s) exists (X). The arrow (→) represents a nucleotide at 3' end of the primers that is complementary to the opposite nucleotide in the template. The parenthesis ( ) denotes that a nucleotide mispair occurred.

The absence of mispair formation and extension at position −99 is due to pfu 3'→5' exonuclease proofreading activity that sharply peaks up at its optimal polymerization temperature, removing the mismatched nucleotide added at the initiation step of primer extension. It is apparently different from the 3'→5' exonuclease proofreading activity of other DNA polymerases such as pol-a and T4 in the primer mispair extension reaction. The mispair at the initiation site of DNA synthesizing can be produced with high frequency by these DNA polymerases in the primer mispair formation and extension reaction (Perinno, F., et al., *Proc. Natl. Acad. Sci. USA.* 86:8343–8347, 1989; Reha-Krantz, L. J., et al., *Proc. Natl. Acad. Sci. USA.* 88:2417–2421, 1991).

Taq DNA polymerase without 3'→5' exonuclease proofreading activities is used in virtually all PCR-based genotyping assays (Okamoto, H., et al., *J. Gen. Virol.* 73: 673, 678, 1992; Newton, C. R., et al., *Nucl. Acids Res.,* 17: 2503–2516). The unreliability caused by cross-reactivity and wrong priming has been a big concern (Lau, J. Y., et al., *J. Infect. Dis.* 171: 281–289, 1995; and Forns, X., et al., *J. Clin. Microbiology.* 34–10: 2516–2521, 1996). When Taq is used instead of pfu, with the other conditions of the assay being the same, the primer 1BR extension took place on template 1a despite a mismatched pair existing at primer extension initiation site (−99) (FIG. 1, column III-2). This clearly indicates that the major cause of these nonspecific reactivities is due to the infidelity of Taq during the initiation of DNA synthesis (Perinno, F., et al., *Proc. Natl. Acad. Sci. USA.* 86: 8343–8347,1989).

In addition, since most DNA polymerases including Taq and reverse transcriptase of retroviruses exhibit a nontemplate-dependent DNA synthesis activity, for example, terminal deoxynucleotide transferase activity ("TDT"), several more nucleotides can be added to the 3' end of the primer, for example, single strand DNA (Clark, J. M., *Nucleic Acids Res.* 16: 9677; Patel, P. H., et al., *Proc. Natl. Acad. Sci. U.S.A.* 91: 549–553). Thus, Taq would be able to continue synthesizing DNA by addition of a correct paired nucleotide next to the mispaired nucleotide, in particular, to the nucleotide in the A:C mispair that can be formed and extended more efficiently than other mispairs (Perinno, F., et al., *Proc. Natl. Acad. Sci. USA.* 86: 8343–8347, 1989; Newton, C. R., et al., *Nucl. Acids Res.* 17: 2503–2516). A DNA strand with mismatched nucleotides would be generated and then act as a template that would be subsequently re-amplified, generating a large number of nonspecific DNA molecules. Therefore, the nonspecific reaction cannot be completely avoided with the methods based on DNA amplification with primer-specific PCR using Taq DNA polymerase. In contrast, in PSMEA, only a single primer is used, so that the extended primer cannot be re-amplified, and any mispairs, including A:C in front of the 3' end of the primer, could completely stop primer extension. TLI/Vent DNA polymerase exhibits 3'→5' proofreading exonuclease activity; however, unlike pfu, TLI/Vent severely degraded single-stranded DNA, for example, a primer, in PSMEA.

In FIG. 1, column I-1, primer extension was performed using pfu with labeled primers (FIG. 1, column I-1), pfu with labeled dNTPs (FIG. 1, column II-1), and Taq with labeled primers (FIG. 1, column III-1). The symbol ↑ represents where the nucleotide incorporation starts. The symbol (X) denotes a stop of primer extension caused by the nucleotide mispair(s).

Figure 2:
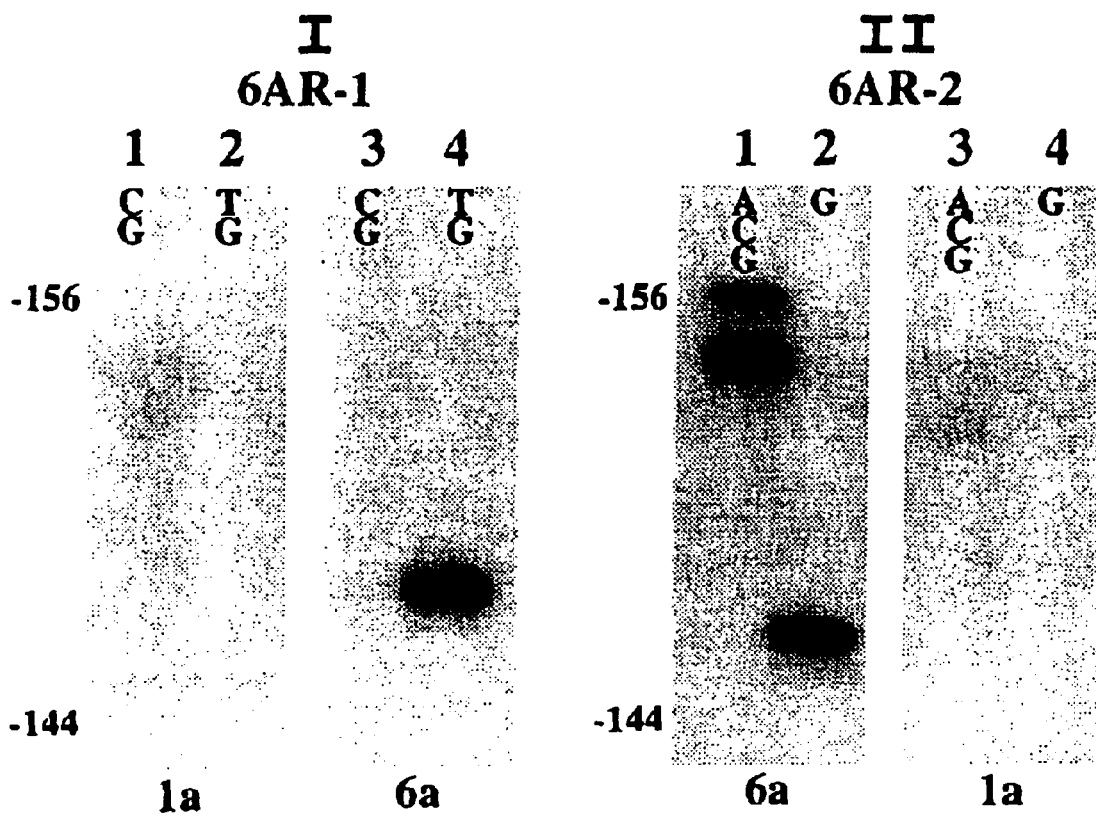

The second feature of specific and mispair extension by pfu is that one correct pairing followed by more than one mispair in front of the 3' end of the primer is not sufficient for primer extension (FIG. 2, columns I-1 and I-2). At least two consecutive correct pairings are required (FIG. 2, columns I-4 and II-2). This provides a means to identify nucleotide deletion and insertion as well as multiple nucleotide variations or mutations in PSMEA.

In FIG. 2, Primer 6AR-1 could not be extended with template HCV genotype 1a when using either dCTP plus dTTP, or dCTP plus dGTP as substrates due to a CA deletion ( . . . ), resulting either in a mispair at nucleotide position −145 in front of the 3' end of primer (FIG. 1, column I-1) or in only one matched pairing at the position (FIG. 1, column I-2). Primer 6AR-1 could not be extended on template HCV genotype 6a when using dCTP and dGTP (FIG. 1, column I-3). However, the primer was extended by three bases with template HCV genotype 6a using dGTP and dTTP which matched the nucleotides in the CA insertion (CA) in template HCV genotype 6a (FIG. 1, column I-4). Primer 6AR-2 was extended when using template HCV genotype 6a (FIG. 1, columns II-1 and II-2), but not with template HCV genotype 1a using either dATP, dCTP and dGTP or only dGTP (FIG. 1, columns II-3 and II-4). The symbol ⇒denotes the removal of the first nucleotide mismatched at the 3' end of the primer.

As seen in FIG. 2, there is a unique CA insertion in the 5' UR of HCV genotype 6a. Use of the CA insertion can differentiate between HCV genotype 6a and other genotypes. In the instant application, the CA insertion is used as an example to show how nucleotide deletion and insertion could be identified. Based on the flanking nucleotide sequence of the CA insertion, two primers were designed. A first primer 6AR-1, located in the region before a CA insertion in HCV genotype 6a, was extended only when using the correctly paired dNTPs, for example, dGTP and dTTP (FIG. 2, column I-4), but not those dNTPs (dCTP and dGTP) (FIG. 2, column I-3) that mismatched with the nucleotide A in the CA insertion The second primer 6AR-2 was designed with the first nucleotide at its 3' end being matched with the first nucleotide A in the CA insertion of template HCV genotype 6a. Thus, the primer extended two bases or 11 bases on template HCV genotype 6a, depending on the substrates of dNTPs used (FIG. 2, columns II-1 and II-2), but not on template HCV genotype 1a due to a CA deletion that results in a 3' mispaired residue being removed after primer binding (FIG. 2, columns II-3 and II-4).

In accordance with the present invention, multiple nucleotide variations or mutations can be identified. For example, a unique TCA motif that is specific to HCV genotype 3a and 3b could be identified and is used for differentiation between the two genotypes and other genotypes.

Like mispair formation and extension by T4 DNA polymerase (Wilber, J. C., et al., M. S. Reverse transcriptase-PCR for hepatitis C virus RNA, p. 327–331; D. H. Persing, T. F. Smith, F. C. Tenover, and T. J. White (ed.), Diagnostic Molecular Microbiology: Principles and Applications, American Society for Microbiology, Washington D.C. 1993), any two or more consecutive mispairs could completely terminate primer extension by pfu because of its 3'→5' proofreading activity (FIG. 1, column II-2 and FIG. 2, columns I-3 and II-2). It was also found that two or more mispairs, separated by one or two correct base pairs (FIG. 1, column II-1 and FIG. 2, column II-1) could also terminate primer extension by pfu. Use of the termination point caused by these mispairs, as well as primer-specific and mispair extensions on templates by pfu, provided reliable information on nucleotide sequence in the given region of the 5' UR of HCV.

The highest molecular weight band shown on the sequencing gels represents the longest sequence extended to the termination point that is specific to each of the HCV genotypes. As indicated in FIG. 1, column II, for example, the highest band represents the primer 1AB extended to the nucleotide C at nucleotide position −100 before the termination point at position −99 and −98 that would produce two mispairs with the two adjacent nucleotides A in template HCV genotype 1a, while the highest band represents the primer extended to the nucleotide G at −99 before the termination point at position −98 and −96 in template HCV genotype 1b, showing the single nucleotide difference between HCV genotypes 1a and 1b. This is another way to identify a single point mutation or variation in PSMEA in accordance with the present invention.

Whatever dNTPs, for example, one two or three of the four dNTPs, are chosen, they must follow the "instruction" with the characteristics of primer-specific and mispair extension by pfu.

The nucleotide incorporation rate of pfu is one fifth (⅕) of that of Taq. Thus, pfu-based PCR applications require a minimum extension time of 2.0 minutes/kb. The efficiency of nucleotide incorporation by pfu is high enough for PSMEA in which only less than 20 bases of extension are required per cycle in the reaction. Over 50% of the excess primer with less template (molecular ratio of primer and template 10:1) could be extended in a 20 cycle reaction, generating strong signals with either $^{32}$P-labeled primer or dNTPs. Thus, PSMEA offers not only an advantage of superior accuracy over current indirect DNA genotyping systems, but an extraordinary sensitivity for detection of mixed infections with different genotypes of HCV.

Figure 3:
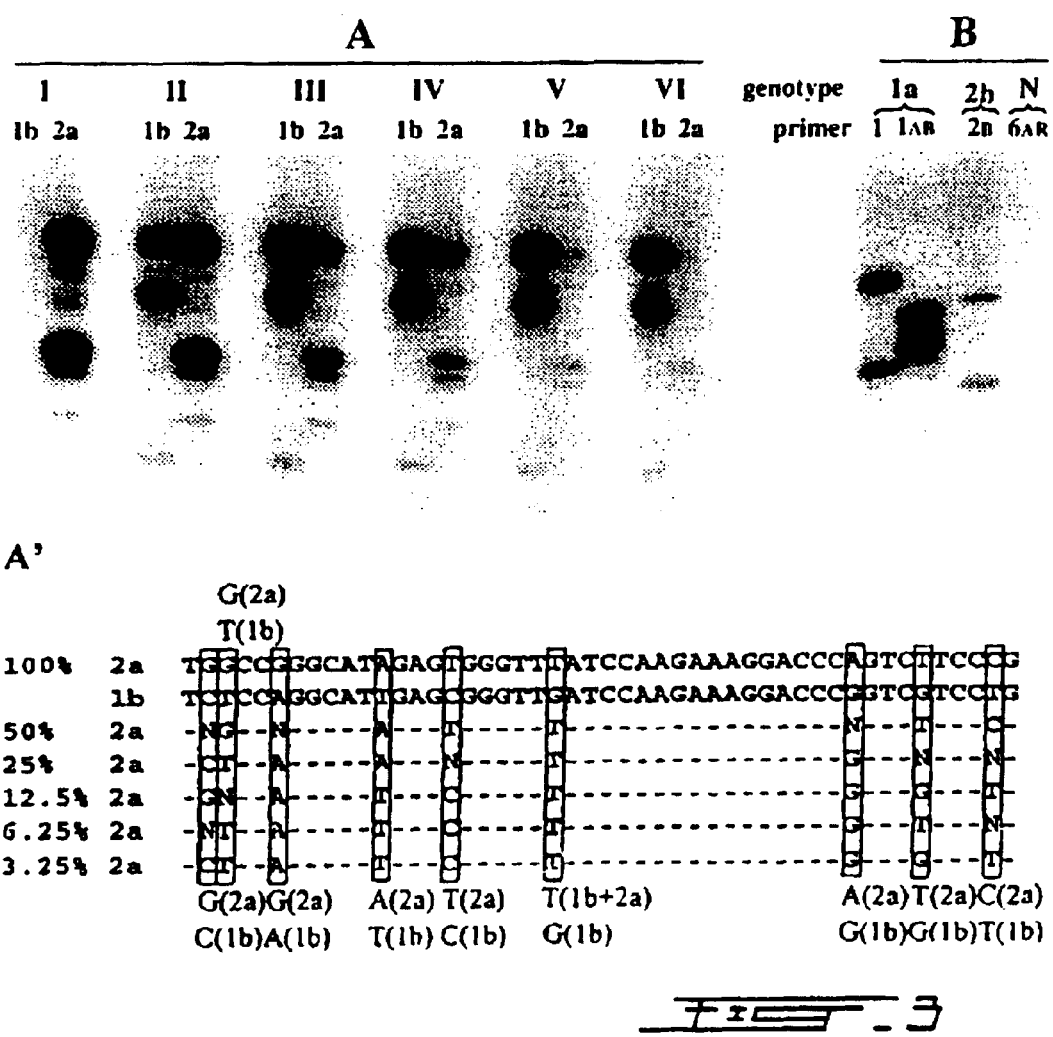
FIG. 3 illustrates a comparison of the sensitivity between PSMEA and direct DNA sequencing in detection of mixed genotypes.

Direct DNA sequencing is routinely used as the gold standard method for confirmation of the results from other assays (Tuveri, R., et al., Journal of Medical Virology 51: 36–41, 1997; (Forns, X., et al., J. Clin. Microbiology. 34–10: 2516–2521, 1996). In the present application, the sensitivity of PSMEA for identifying mixed infections was evaluated with direct DNA sequencing methods. In an experiment, the cDNAs (PCR products) from HCV genotypes 1b and 2a isolates were mixed in different proportions to mimic HCV mixed infections and heterozygotes. FIG. 3 shows that HCV genotype 2a could be clearly identified by direct DNA sequencing only when it reached to 50% in proportion in the mix. When HCV genotype 2a molecules consisted of less than 25%, only some of nucleotide variation, points could be manually recognized but was not conclusive for the identification of which genotype it was. However, HCV genotype 2a consisting as low as about 3% in the mix was clearly detected by PSMEA, showing approximately 10 times more sensitivity than the direct DNA sequencing system.

To further confirm the sensitivity of PSMEA, three samples identified having two or three genotypes by PSMEA were analyzed by direct DNA sequencing (FIG. 3, column B) and the reverse hybridization method. Results reveal that the presence of HCV genotype 2b was confirmed by the direct DNA sequencing method, but not by the reverse hybridization method in the sample containing 1a as dominant population.

FIG. 3 presents autoradiography results in column A and the date of a computer analysis of automated sequencing in column A'. FIG. 3, part A, illustrates the different proportions of genotypes 1b and 2a: 0% to 100% (I), 50% (II), 75% to 25% (III), 87.5% to 12.5% (IV), 93.75% to 6.25% (V), and 96.875% to 3.125% (IV) in the mix analyzed with PSMEA FIG. 3, part A and direct DNA sequencing FIG. 3, part A'. Two HCV genotypes, 1a and 2b, were identified in a thalassaemia patient sample by PSMEA FIG. 3, part B. N in FIG. 3, part B represents the negative reaction with primer 6AR and the sample from the thalassemia patient.

To evaluate the feasibility of PSMEA for large cohort studies, a total of two hundred and forty-five (245) samples from HCV seropositive blood donors and patients with chronic hepatitis were genotyped by this assay. The genotypes determined by PSMEA included 1a, 1b, 2a, 2b, 2c, 3a, 3b, 4, 5a and 6a. The typeable rate of these samples with PSMEA was 95.5%. Eighty (80) of them were also typed with other indirect or direct DNA sequencing genotyping methods. The genotyping results from PSMEA were in 90–100% concordance with that from other genotyping methods including LiPA, RFLP and direct DNA sequencing. Less than 5% of untypeable samples were sequenced, indicating that those isolates being untypeable by PSMEA were either HCV mutants or unclassified genotypes. Results have proven a great utility of PSMEA for large cohort studies on viral genotyping.

PSMEA has been further developed with an automatic and colorimetric format, creating a great capacity to quickly genotype a large number of HCV isolates not previously possible. Therefore, PSMEA has a great potential for identifying nucleotide variations and heterozygotes in many areas such as virology, bacteriology, human genetics, epidemiology and legal medicine.

When a type- or subtype-specific sequence is available for designing the primer, for example primers 2A and 3A, no cross-reactivities with other genotypes are observed in PSMEA. Consistent results were obtained with primers 1AB, 2B, 2C, and 3R (Table 2).

Primer 1AB is universal for HCV genotypes 1a and 1b (FIG. 1, column III), differentiating the two genotypes from other genotypes except genotype 6a due to the homologous sequence in the region −131 and −99 between genotypes 1a/1b and 6a. Fortunately, a nucleotide A in the unique CA insertion between the nucleotide positions −145 and −144 in the 5' UR of 6a could be used as a first paired nucleotide at the 3' end of primer 6AR, thus, the primer specifically extended on template 6a, but not on other genotypes (FIG. 2, column I).

The primer could be bound on other genotypes, but could not be extended due to the CA deletion in these genotypes as compared with the insertion in 6a 5'UR. It was thus found that, for example, the primer 6AR-1 could not be extended because there was a single C at position−145 which could be paired in the presence of dTTP and dGTP, followed by three Ts in the template HCA genotype 1a, in the reaction (FIG. 2, column I-1). However, the primer extended on template 6a in the same reaction conditions due to the presence of the two consecutive pairings C:G and A:T at positions between −145 and −144 (FIG. 2, column I-4). Accordingly, the primer 6AR2 could be extended longer on template 6a when using three dNTPs (dATP, dGTP and dCTP), showing a stronger signal to differentiate 6a from other genotypes (FIG. 2, column II-1). In the same manner, primer 5AR designed with a nucleotide variation at −236 was subtype-specific.

As shown in Table 2, primer 3B, that was originally designed for identification of genotype 3b, exhibited cross-reactivity with 4e in PSMEA due to the homologous sequence in the region −175 to −149 chosen between the two genotypes. Thus, a small region (−99 to −79) that contains a unique TCA motif in 5'UR of genotypes 3a and 3b was used for designing the primer 3R. Thus, by using primers 3A and 3R, genotypes 3a and 3b could be differentiated from other genotypes. Similarly, three genotypes 1a, 1b and 6a could clearly be identified with primer 1AB, 1BR and 6AR that exhibited a cross-reactivity with 1AB. A total 11 genotypes, including six major genotypes (1a, 1b, 2a, 2b, 3a, 3b) and some uncommon genotypes (2c, 5a, 6a, 4a and 4e), in Canada could be identified by PSMEA using 11 primers (Table 2).

Extension of the mismatched 3' termini of DNA is a major determinant of the infidelity of the DNA polymerases that have no 3'→5' exonuclease activity (Pistello, M. et al., *J. Clin. Microbiol.* 32: 232–234). With the PSMEA of the present invention, by using 3'→5' exonuclease proofreading activity, high detection specificity for nucleotide mutation or variation in a known gene has been achieved. A significant advantage of this assay is that a single nucleotide variation, deletion and insertion can be accurately detected. In the genome of many natural virus mutants or drug-restistant mutants, there may be only a single nucleotide mutation that has potential genetic or clinical significance. For example, a substitution C for A at nucleotide position 1814 that destroys the precore initiation codon, will prevent production of HBVeAg. In some drug-resistant mutants, a single nucleotide mutation could cause a failure of an antiviral therapy. PSMEA of the present invention can thus be used for rapid screening of those mutants.

A single point mutation could be associated with genetic disease in humans, such as a single point mutation, resulting in an amino acid substitution (C282Y) in the gene, HLA-H for haemochromatosis, which was reported to be involved in iron metabolism disorder. Such single point mutations are frequently found in viruses. For example, a substitution C for A results in loss of precore initiation codon of hepatitis B virus, preventing e-antigen (HBVeAg) synthesis.

The PSMEA of the present invention can be modified so as to replace radioactivity by a detectable label. Such a nonradioactive assay could be in the form of a calorimetric PSMEA in a microtiter-plate format.

The present invention will be more readily understood by referring to the following examples, which are given to illustrate the invention rather than to limit its scope.

EXAMPLE I

Determination of HCV Genotypes

Primer extension reactions contained 20 ng primer, 20–30 ng PCR product, 20 mM of each dCTP and dGTP, 10 mCi of each $^{32}$p-labeled dCTP and dGTP, 1.25 units pfu DNA polymerase and 10 ml 10×pfu reaction buffer (PDI). When 5'-end $^{32}$p-labeled primers were used, the $^{32}$p-labeled dCTP and dGTP were omitted, and 100 μM of each dCTP and dGTP were used in the reactions. The primer extensions were performed in a reaction volume of 100 ml in a thermocycler (Perkin Elmer, GeneAmp 9600). Twenty (20) cycles consisting of a denaturation step at 94° C. for 20 seconds, an annealing step at 64° C. for 20 seconds and an extension step at 72° C. for 35 seconds were performed. One microliter of the primer extension products was mixed with 1 μL of the sequencing stop solution (Pharmacia Biotech) and electrophoresed on 8% polyacrylamide 8M urea TBE gels for one hour. Extension products were visualized by autoradiography.

For PCR amplification and sequence analysis, viral RNA was isolated from 100 ml of serum by treatment with RNAzol B (Biotecx Laboratories, Houston, Tex.) as previously described in Wilber, J. C., Johnson, P. J., and Urdea, M. S. Reverse transcriptase-PCR for hepatitis C virus RNA, p. 327–331, and in D. H. Persing, T. F. Smith, F. C. Tenover, and T. J. White (ed.), Diagnostic Molecular Microbiology: Principles and Applications. American Society for Microbiology, Washington D.C. 1993. RT-PCR was performed as described by Bernier et al. (Bernier, L., et al., *J. Clin. Microbiol.* 34: 2815–1818), with a set of primers that target highly conserved domains within the 5'-UR. The nucleotides and primers were removed from the PCR products with the QIAquick™ PCR Purification Kit (QIAGEN), using the procedure recommended by the product supplier. These purified PCR products were used for primer extension and automated sequencing analysis.

HCV isolates from patients with HCV infection were typed either by the improved Inno LiPA kit II™ using the procedure provided by the supplier (Innogenetics N.V., Belgium) or by RFLP analysis. For RFLP analysis, HCV genotypes were determined by cleavage of the PCR products with restriction enzymes BstNI, Bsr, Hinfl, Maelll, Haelll, BstUl and ScrFl. Digests were analyzed by gel electrophoresis and ethidium bromide staining.

EXAMPLE II

Primer Design and PSMEA Procedure

In accordance with a preferred embodiment of the invention, the development of PSMEA is based on a single primer extension in the 5'-UR of the HCV genome using pfu DNA polymerase in the presence of only dCTP and dGTP in the reaction. Thus, under these reaction conditions, primer extension occurs when only the G and/or C nucleotides are added immediately downstream of the 3' end of the primer, since the incorporation of A or T nucleotide would in many instances be prevented by the 3'-5' exonuclease activity of pfu. The primers were designed to meet the following requirements:

1. They must have type-specific sequences; and
2. All primers used for PSMEA should exhibit a similar melting temperature.

The nucleotide sequences of the primers used in this study are shown in Table 1. In the PSMEA procedure, the primer extension reactions contained 20 ng primer, 20–30 ng PCR product, 20 mM of each dCTP and dGTP, 10 mCi of each $^{32}$P-labeled dCTP and dGTP, 1.25 units pfu DNA polymerase and 10 ml 10×pfu reaction buffer (Stratagene). When 5'-end $^{32}$P-labeled primers were used, the $^{32}$P-labeled dCTP and dGTP were omitted, and 100 μM of each dCTP and dGTP were used in the reactions. The primer extensions were performed in a reaction volume of 100 ml in a thermocycler (Perkin Elmer, GeneAmp 9600). Twenty cycles of 94° C. for 20 seconds, 64° C. for 20 seconds and 72° C. for 35 seconds were performed. One microliter of the primer extension products were mixed with 1 μL of the sequencing stop solution (Pharmacia Biotech) and electrophoresed on 8% polyacrylamide 8M urea TBE gels. Extension products were visualized by autoradiography.

EXAMPLE III

PCR Amplification and Sequence Analysis

Viral RNA was isolated from 100 ml of serum by treatment with RNAzol B (Biotecx Laboratories, Houston, Tex.) as previously described in Wilber, J. C., Johnson, P. J., and Urdea, M. S. Reverse transcriptase-PCR for hepatitis C virus RNA, p. 327–331, and in D. H. Persing, T. F. Smith, F. C. Tenover, and T. J. White (ed.), Diagnostic Molecular Microbiology: Principles and Applications. American Society for Microbiology, Washington D.C. 1993. RT-PCR was performed as described by Bernier, L., et al., *J. Clin. Microbiol.* 34: 2815–1818, with a set of primers (see Table 1) that target highly conserved domains within the 5'-UR. If a second round PCR was necessary to provide sufficient cDNA for PSMEA, a pair of nested primers (sense primer –211 to –192 and antisense primer –91 to –74) was used. The nucleotides and primers were removed from the PCR products with the QIAquick™ PCR Purification Kit (QIAGEN), using the procedure recommended by the manufacturer. These purified PCR products were used for PSMEA and for automated sequencing analysis.

EXAMPLE IV

Genotyping of HVC Isolates by LiPA and RFLP

HCV isolates from patients with HCV infection were typed either by the improved Inno LiPA kit II™ using the procedure provided by the supplier (Innogenetics N.V., Belgium) or by RFLP analysis. For RFLP analysis, HCV genotypes were determined by cleavage of the PCR products with restriction enzymes BstNI, Bsr, Hinfl, Maelll, Haelll, BstUl and ScrFl, (Andonov, A., et al., *J. Clin. Microbiol.* 32: 2031–2034, 1994). Digests were analyzed by gel electrophoresis and ethidium bromide staining.

EXAMPLE V

The Accuracy and Reliability of PSMEA

To evaluate the accuracy and reliability of PSMEA, 51 HCV isolates from HCV infected individuals in Montreal, Canada, typed by RFLP analysis in the 5' UR (Andonov, A., et al., *J. Clin. Microbiol.* 32: 2031–2034, 1994) were analyzed with PSMEA in a double blind study. The subtypes 2a and 2c were grouped together when RFLP was used for genotyping of the 51 isolates, since some 2c variants share common ScrFI cleavage sites with 2a variants.

A primer designed with sequence –133 to –113 from this isolate has shown no cross-reactivity with other types described in the present study (Table 2), suggesting that most isolates determined as 2a/2c by RFLP have a typical 2a-specific sequence, and that the primer 2A can discriminate the majority of subtype 2a from subtype 2c. The results from the analysis of these 51 isolates indicate that 100% of types and subtypes for the isolates determined by PSMEA were matched with the types and subtypes identified with RFLP. In these isolates, there were 14-1a, 14-1b, 5-2a, 5-2b, 1-2c, 10-3a, 1-3b, and 1-6a. LiPA was reported to reliably type the most common genotypes, including some subtypes (Simmonds, P., Variability of Hepatitis C. Virus. *Hepatology* 21: 570–582, 1995). Fifteen (15) isolates were typed by LiPA and evaluated with PSMEA in accordance with the present invention. They include 5-1a, 6-1b, 1-2a, 1-2b, 1-3a, 1-3b. The results from PSMEA showed a 100% agreement with that from LiPA.

A group of five (5) HCV isolates that failed to be typed or subtyped by other methods were clearly identified as 1a or 1b by PSMEA. The results were confirmed by direct DNA sequencing using their PCR products from the 5' UR region (–211 to –71) (FIG. 4), suggesting that results from PSMEA is reliable.

In the present application, the majority of the samples were typed with PSMEA using nonlabeled primers and $^{32}$p-labeled dNTPs. Results obtained using $^{32}$p-labeled dNTPs with unlabeled primers showed the typical patterns of the primer extensions as seen in the results from the reaction with $^{32}$p-labeled primers and nonlabeled dNTPs.

Accordingly the new genotyping assay, primer-specific and mispair extension assay (PSMEA), of the present invention was used to genotype HCV and to detect mixed infections. A total of one hundred and forty-six (146) HCV isolates were typed and analyzed with PSMEA, showing that nine of 110 isolates (8.2%) from HCV positive blood donors and six of 36 isolates (16.7%) from thalassaemia patients were found to contain more than one genotype. The results were confirmed and compared with other current assays including direct DNA sequencing and line probe assay (LiPA). PSMEA of the present invention was found to be more reliable than other assays in detecting mixed infection.

EXAMPLE VI

Feasibility of PSMEA for Large Cohort Studies

Some genotypes including 1a, 1b, 2a, and 2b show a broad geographical distribution, and the infection frequency of subtypes 1a and 1b can be over 50% in blood donors and patients with chronic hepatitis in the United States (Lau, J. Y., et al., *J. Infect. Dis.* 171: 281–289, 1995), Canada (Bernier, L., et al., *J. Clin. Microbiol.* 34: 2815–1818, and Andonov, A., et al., *J. Clin. Microbiol.* 32: 2031–2034, 1994), and most European countries (Simmonds, P., *Hepatology* 21: 570–582. 1995, and Stuyver, L., Rosseau, et al., *J. Clin. Microbiol.* 34: 2259–2266, 1996). Other genotypes, such as 3a and 3b are less common than 1a and 1b in those countries. However, 3a seems to be quite frequently found in Canada. Genotypes 4, 5a and 6a are only found in specific geographical regions in the Middle East, South Africa and Hong Kong, respectively, but were also infrequently found in some areas of Canada. It is apparent that for each region, a strategy for genotyping a large number of HCV isolates by PSMEA has to be designed, based on the genotype distribution and infection frequency with the population. For example, in Canada, over 60% of HCV isolates are genotypes 1a, 1b, which can be identified by primers 1AB, 1BR.

However, since genotype 6a was frequently found in some areas of Canada and primer 1AB was cross-reacted with 6a, thus all isolates diagnosed as 1a should be retested with primer 6AR for screening of genotype 6a in the first round of testing with PSMEA. The nontypeable isolates using the three primers should be retested with primers 2A and 2B. Thus, genotypes 2a and 2b (over 15% of total isolates) can be determined in the second round of testing. The remaining nontypeable isolates should be screened with primers 3A, 3B and 3R. Genotypes 3a and 3b (over 15% of total isolates) can be identified in the third round of testing. After the third round of testing, the rest of the isolates (less than 10% of total isolates) that cannot be typed by these primers would include some subtypes of type 4, subtype 5a, subtype 2c or other genotypes. Table 3 identifies the infection frequencies of the major HCV genotypes identified by PSMEA, indicating that it is practical and feasible for genotyping a large number of isolates for epidemioloy and clinical studies.

All current genotyping assays such as those for HCV, including direct DNA sequencing, are not suitable for detection of mixed infections because they are designed for detection of the population-dominant genotype. As indicated in Table 3, HCV mixed infection rate was higher than expected. A reliable detection of HCV mixed infections by PSMEA in different populations with HCV infection is thus reported.

EXAMPLE VII

Determination of HIV-1 Mutants

HIV positive sequential plasma samples were collected from patients on the combination therapy with RT and protease inhibitors for greater than three months Viral RNA from samples was purified using the QAamp™ Viral RNA kit. The Pharmacia Biotech First-Strand cDNA Synthesis kit was then used for cDNA synthesis. PCR was performed to amplify the region containing the entire protease and RT regions of HIV-1. The PCR products were purified using the QIA quick™ PCR Purification kit for genotypic analysis with PSMEA, direct DNA sequencing and cloning.

PSMEA was performed with the procedure described above. This assay has been developed as a semi-automated system. Accordingly, a Cy5.5 dye-labeled primer (at the 5'-end of the primer) was used instead of a $^{32}$P-labeled primer. Primer extension reactions contained 20 ng of 5'-end 5.5 dye-labeled primer, 20–30 ng of PCR product, 20 µM of each dNTP, 1.25 units of pfu DNA polymerase and 10 µL of 10× pfu reaction buffer (PDI). Primer extensions were performed in a 100 µL reaction volume in a thermocycler (Perkin Elmer, GeneAmp 9600). Twenty cycles of 94° C. for 20 seconds, 64° C. for 20 seconds and 72° C. for 35 seconds were performed. One microliter of the primer extension products was mixed with 1 µL of the sequencing stop solution (Pharmacia Biotech) and electrophoresed on 6% polyacrylamide 8M urea TBE mini gels for 10 minutes. Extension products were analyzed by automated DNA fragment length polymorphism analysis software in the Open-Gene™ automated DNA sequencing system (Visible Genetics).

Both direct DNA sequencing and population based sequencing were performed with an automated DNA sequencer (Visible Genetics) and DNA sequencing kits (Visible Genetics). For the population based DNA sequencing, the PCR products were directly cloned into the TOPO™ TA vector (Invitrogen Corp.). The TTV sequence was amplified from positive colonies of *Escherichia coli* using M13 primers (Pharmacia Biotech). The re-amplified PCR products were sequenced using the same procedure as used for direct DNA sequencing.

Figures 5A, 5B:
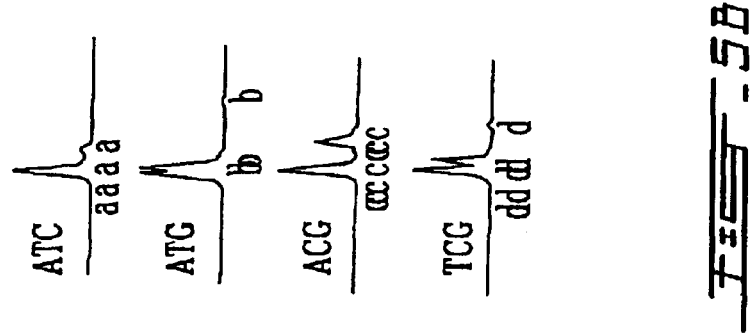
FIGS. 5A and 5B illustrate the detection of HIV-1 drug-resistant mutant V82A and wild type V82 using a universal primer and four sets of dNTPs.

Based on the principle of PSMEA, primers can be designed to be either universal for both wild type and mutants or type-specific, for example, specific to either wild type or mutants. In addition, many options can be explored with different sets of dNTPs and locations of primer binding. To test the feasibility of PSMEA for HIV-1 genotyping, the three most common and important mutation sites of codons 82 (V82), 63 (L63) and 90 (L90) were detected by PSMEA and direct DNA sequencing. FIGS. 5A and 5B show an example to indicate the primer design and expected base extensions using different sets of dNTPs for detecting mutation of V82A with a universal primer. In FIGS. 5A and 5B, each combination of dNTPs results in a different extension profile, providing a fingerprint for wild type and mutant. In FIG. 5A, extension profiles for wild type and mutant are illustrated. In FIG. 5B, the peak profiles represent the number of bases extended as detected by automated DNA sequencing using fragment length polymorphism analysis software, with the first peak from left representing unextended primer. When using specific sets of dNTPs, ATC, ATG, ACG and TCG, the primer will extend 3, 1, 0 and 2 bases with wild type. In contrast, extensions of 0, 1, 5, and 2 bases will occur with mutant. These results clearly indicate that the predominant population in this sample was V82A mutant, showing a pattern of 0, 1, 5 and 2 bases extended. However, in the presence of ATC, about 12% of the primer extended, indicating a low proportion of the wild type virus still remained in this patient. Apparently only two sets of dNTPs (ATC and TCG) were needed to determine the levels of mutant and wild type in a mix. In some cases, V82 could mutate to V82I instead of V82A. A primer was designed for detection of V82I mutation using a set of dNTPs (A, T, and C).

Figure 6B:
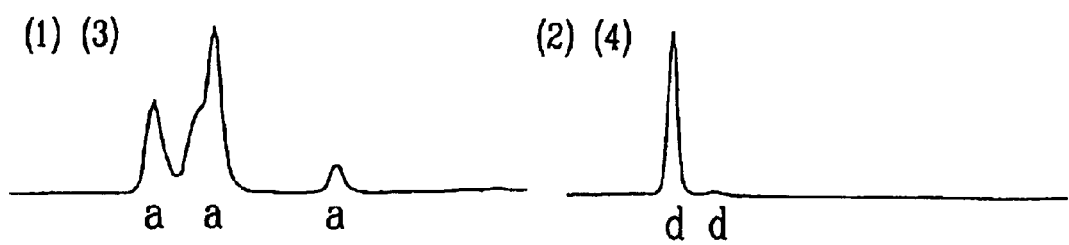

It is more difficult to detect drug-resistant mutations at codon 63 than other sites because in this case there are 6 combinations of codons for Leucine (L63) and 4 codons for Proline (P63). Since a wild type/mutant mix would almost certainly be caused by a single base substitution, only four variations should be expected, with only CTC/CCC (L63) and CTT/CCT combinations seen so far, with the former combination being the most common. To overcome this problem, a new type of primer was designed for PSMEA to detect different drug-resistant mutations of L63 codon as follows: the target mutation point was included as part of the 3' end of two primers. The 3' end of one primer (PRO63L (G)-R) was a perfect match to the wild type, but not mutant (FIGS. 6A(1) and 6A(2)), while the 3' end of the second primer (PRO63P(G)-R) was a perfect match to the nucleotide sequence of mutant, but not wild type (FIGS. 6A(3) and 6A(4)). In FIG. 6A, the matched primers should have 4 and 14 bases extension on both L63 and L63P ((1) and (3)), and the primers with mispairs on L63P and L63 were expected to have no extension (FIG. 6A, parts (2) and (4)). In FIG. 6B, the primer extended either 4 and 14 bases (second and last peaks from the left) FIG. 6A, parts (1) and (3), or virtually not at all (FIG. 6A, parts (2) and (4)).

If a mismatch occurs on the 3' end of the primer, the pfu will remove the mismatched nucleotides. A mix of 3 dNTP's was added to the reaction in which there are no dNTPs to correct the mismatches on the 3' end of the primer. Thus, primer extension occurs under these circumstances only if the 3' end of the primer was a perfect match to the target mutation point. This results in very little, if any, nonspecific extension, even at annealing temperatures as low as 55° C. When dNTPs (A, T and C) were added, the matched primer was extended with 5 and 14 bases extensions (FIG. 6A, parts (1), (2), and (3) and FIG. 6B, parts (1) and (3)). However the mismatched primer could not be extended because the mismatched nucleotides at 3' end of the primer were removed with no dGTP to repair the mismatch (FIG. 6A, parts (2) and (4) and FIG. 6B, parts (2) and (4)).

Unlike protease codon 63 which has multiple combinations for L63 mutating to L63P, and codon 82 with V82 mutating to V82I/A/others, codon 90 has only one possible combination for L90 mutating to L90M (AAG to ATG). As a result, only one pair of primers is required for detection of this mutation point. FIGS. 7A and 7B show that the primer (PRO90L-R) was designed in a reverse direction for detection of L90. FIG. 7A illustrates the expected number of bases extended with matched and mismatched primers on wild type and mutant, respectively (1–4). In FIG. 7B, primers PRO90L-R and PRO90M-F on wild type were extended with 4 on wild type (1) and 8 bases on mutant (3).

As expected, the primer was extended with four bases (FIG. 7A, part (1) and FIG. 7B, part (1)). Under the same reaction conditions, the primer was not extended on mutant L90M due to the T:T mismatch at the 3' end of the primer (FIG. 7A, part (2) and FIG. 7B, part (2)). Another primer (PRO90M-F) was designed to detect low levels of drug-resistant mutant L90M. The primer was extended on L90M mutant with eight bases (FIG. 7A, part (3) and FIG. 7B, part (3)), but not on wild type due to the second to last nucleotide mismatch (A:A) at the 3' end of the primer (FIG. 7A, part (4) and FIG. 7B, part (4)).

Figure 8:
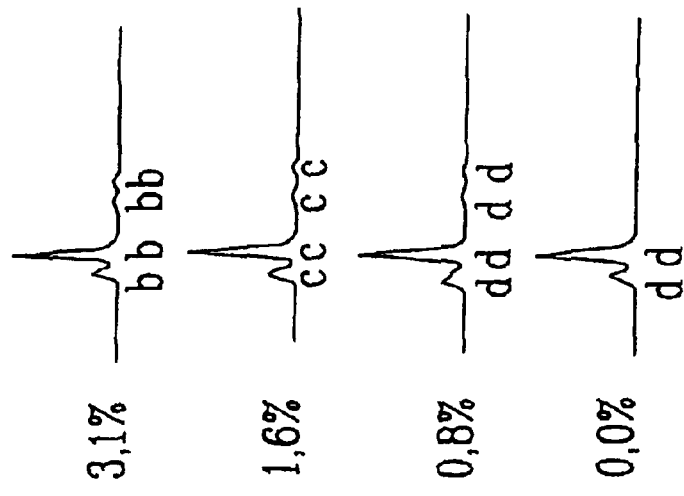
FIG. 8 illustrates the sensitivity of PSMEA for detecting low levels of HIV-1 drug-resistant mutant with a defined mix of mutant V82I and wild type V82.

In order to assess the sensitivity of PSMEA for detecting low levels of mutants in a viral population, an artificial mixing experiment was carried out. PCR products from the protease region of V82 wild type and the V82I mutant were mixed in the following proportions between mutant and wild type: 3.1% (1/32), 1.6% (1/64), 0.8% (1/128) and 0.0% (for example, 100% wild type). FIG. 8 shows that 0.8% mutant in the mix was clearly detected with PSMEA. The levels at 0.8%–3.1% were not detected by direct DNA sequencing. It has previously been reported that the mixed genotypes or quasispecies could be detected only when mixed genotype (s) reached levels over 25% (Deeks S G, Abrams D I., *Lancet,* 349: 1489–1490, 1997).

To confirm the sensitivity of PSMEA, a total of 32 isolates from patients being treated with antiviral drugs have been analyzed with both direct DNA sequencing and PSMEA for the presence of drug-resistant mutations in codon V82, L63 and L90 from the protease region of HIV-1. Table 4 shows a 100% concordance of the genotypic testing results between PSMEA and direct DNA sequencing for detection of predominant population of variants including mutants and wild type.

Twenty-five (25) (78.1%) of 32 samples determined as being fully wild type (V82) were found to contain either mutants V82I or V82A at various levels (1–19%). Different levels (3–27%) of L63P mutant were detected by PSMEA in 100% (5/5) of the samples that were determined as purely wild type (L63) by direct DNA sequencing. However, in detecting L90M mutation, the results showed 86.7% (13/15) concordance between the two methods.

One of the samples (AR283) was analysed using population based sequencing, direct DNA sequencing and PSMEA to further evaluate the accuracy of PSMEA in detecting low levels of drug-resistant mutants. Table 5 shows that PSMEA demonstrated greater concordance with population based sequencing than direct DNA sequencing for monitoring minor variants. Seventy-six percent (76%) and twenty percent 20% of isolate from AR283 was found to be V82I mutant and wild type V82, respectively, by PSMEA, but 100% mutant V82I by direct DNA sequencing. Population based sequencing showed that wild type truly existed at a level of 12.5% (4/32). For detection of predominant populations variants (mutant V82I and wild type L90) in the isolate, both direct DNA sequencing and PSMEA were 100% concordant with population based sequencing.

From the above, it is thus apparent that PSMEA is more sensitive than direct DNA sequencing for detection of low levels of drug-resistant mutants. The high degree of sensitivity of PSMEA should allow one to more precisely understand how early drug resistant mutations can develop, especially during antiretroviral therapy. For clinics, this may further aid in guiding clinicians in modulating therapeutic regimens before the appearance of phenotypic drug resistance or deterioration in clinical status. With early warning of drug specific mutations, agents can be chosen to impede resistance and minimize cross-resistance, yet still have an antiviral effect on the patient's dominant quasispecies. This, in turn, will hopefully delay therapeutic failure and increase survival.

TABLE 1

Nucleotide sequence of the primers for PSMEA

| Primers | Position | Sequence from 5 to 3 |
|---|---|---|
| For PCR (universal) | | |
| 1st round | −302 to −278 | CTC CCC TGT GAG GAA CTA CTG TCTT (sense) (SEQ. ID. NO. 1) |
| | −50 to −31 | CTC GCA AGC ACC CTA TCA GG (Antisense) (SEQ. ID. NO. 2) |
| 2nd round | −204 to −175 | CCA TAG TGG TCT GCG GAA CCG GTG AGT ACAC (Sense) (SEQ. ID. NO. 3) |
| | −91 to −74 | CCC AAC ACT ACT CGG CTA (Antisense) (SEQ. ID. NO. 4) |
| For PSMEA | | |
| 1AB | −131 to −111 | CTC AAT GCC TGG AGA TTT GGG (SEQ. ID. NO. 5) |
| 1 | −76 to −157 | CAC CGG AAT TGC CAG GAC GA (SEQ. ID. NO. 6) |
| 1BR† | −98 to −78 | ACA CTA CTC GGC TAG CAG TCT (SEQ. ID. NO. 7) |
| 2A | −134 to −114 | CCA CTC TAT GCC CGG TCA TTT (SEQ. ID. NO. 8) |
| 2B | −128 to −108 | TAT GTC CGG TCA TTT GGG CAC (SEQ. ID. NO. 9) |
| 2C | −133 to −113 | CAC TCT GTG CCC GGC CAT TTG (SEQ. ID. NO. 10) |
| 3A | −175 to −157 | ACC GGA ATC GCT GGG GTG A (SEQ. ID. NO. 11) |

TABLE 1-continued

Nucleotide sequence of the primers for PSMEA

| Primers | Position | Sequence from 5 to 3 |
|---|---|---|
| 3B | −175 to −157 | ACC GGA ATC GCC GGG ATG A (SEQ. ID. NO. 12) |
| 3R† | −99 to −79 | CAC TAC TCG GCT AGT GAT CTC (SEQ. ID. NO. 13) |
| 5AR† | −236 TO −218 | GGG GGT CCT GGA GGC TGT T (SEQ. ID. NO. 14) |
| 6AR† | −145 TO −125 | CAT TGA CGC GGT TTG ATC AAT (SEQ. ID. NO. 15) |

†Antisense primer

TABLE 2

Identification of HCV genotypes with each of the primers by PSMEA

| | | HCV Genotypes | | | | | | | | | | |
|---|---|---|---|---|---|---|---|---|---|---|---|---|
| | Primers | 1a | 1b | 2a | 2b | 2c | 3a | 3b | 4a | 4e | 5a | 6a |
| Reactivities of the Primers | 1AB | + | + | | | | | | | | + | |
| | 1 | + | + | | | | | + | | | | |
| | 1BR | | + | | | | | + | + | + | | |
| | 2A | | | + | | | | | | | | |
| | 2B | | | * | + | | | | | | | |
| | 2C | | | | | + | | | | | | |
| | 3A | | | | | | + | | | | | |
| | 3B | | | | | | | + | | + | + | |
| | 3R | | | | | | + | + | | | | |
| | 5AR | | | | | | | | | | + | |
| | 6AR | | | | | | | | | | | + |
| Criteria for determination of the genotypes by the positivities of the primers | | 1AB+ 6AR− | 1BR+ 1AB+ | 2A+ | 2B+ 2A+ | 2C+ | 3A+ | 3B+ 3R+ | 1+ 1BR+ | 1BR+ 3B+ | 5AR+ | 6AR+ |

*weak reaction

TABLE 3

The prevalence of HCV mixed genotype infections in different populations determined by PSMEA and direct DNA sequencing

| | PSMEA | Direct DNA sequencing |
|---|---|---|
| Blood donors | 7/72 (9.7%) | ND |
| Patients with chronic hepatitis C | 15/80 (18.8%) | 8/80 (10.0%)# |
| Thalassemia patients | 6/36 (16.7%) | 4/36 (11.1%) |

The samples determined to contain more than one genotype by direct DNA sequencing were 100% concordant with that determined by PSMEA. Since the direct DNA sequencing method is not sensitive enough to detect low levels (<25%) of mixed genotype infections, the percentage of mixed genotype infections determined by direct DNA sequencing is lower than what was found by PSMEA.

TABLE 4

Comparison of the sensitivity between direct DNA sequencing and PSMEA for detecting low levels of drug resistant mutations

| | Direct DNA Sequencing | | | PSMEA | | | |
|---|---|---|---|---|---|---|---|
| Sample ID | L63P/ C/L63T (W/M) | V82/I/A (W/M) | L90/M (W/M) | L63 (%) | L63P/L63C (%) | V82/V82I/V82A (%) | L90/L90M (%) |
| 4B | L63 | V82 | L90 | | | 91  7  2 | |
| 6B | L63P | V82 | L90 | 3 | 97P | 96  2  2 | |
| 7B | L63C | V82 | L90 | | | 83  14  3 | |
| 8B | L63P | V82 | L90 | 2 | 98P | 89  3  8 | |
| GL | L63P | V82 | L90M | | | 97  <1  2 | 7  93 |
| JB | L63P | V82A/V | L90M/L | | | 31  15  54 | 56  44 |

TABLE 4-continued

Comparison of the sensitivity between direct DNA sequencing and PSMEA for detecting low levels of drug resistant mutations

| Sample ID | Direct DNA Sequencing L63P/ C/L63T (W/M) | V82/I/A (W/M) | L90/M (W/M) | PSMEA L63 (%) | L63P/L63C (%) | V82/V82I/V82A (%) | | | L90/L90M (%) | |
|---|---|---|---|---|---|---|---|---|---|---|
| MN | L63P | V82A | L90M | 0 | 100P | 22 | 10 | 68 | 5 | 95 |
| CA | L63P | V82 | L90 | 0 | 100P | 89 | 9 | 2 | 100 | 0 |
| DS1 | L63P | V82 | L90 | | | 86 | 12 | 2 | | |
| DS2 | L63P | V82 | L90 | 3 | 97P | 95 | 3 | 2 | | |
| GP | L63P | V82 | L90 | | | 91 | 3 | 6 | 100 | 0 |
| AS | | V82A | | | | 14 | 4 | 82 | | |
| FP | L63P | V82 | L90 | | | 90 | 7 | 3 | 100 | 0 |
| M15-8 | L63C | V82 | L90 | 49 | 51C | 93 | 5 | 2 | | |
| M15-10 | L63 | V82 | L90 | 73 | 27C | 90 | 6 | 4 | | |
| M17-17 | L63C | V82V/I | L90 | 50 | 50C | 71 | 27 | 2 | | |
| M17-22 | L63C | V82 | L90 | 48 | 52C | 90 | 8 | 10 | | |
| M17-25 | L63 | V82 | L90 | 88 | 12C | 54 | 17 | 29 | | |
| M17-33 | L63T | V82 | L90 | | | 84 | 14 | 2 | | |
| M17-35 | L63T | V82 | L90 | | | 81 | 16 | 3 | | |
| M17-37 | L63 | V82 | L90 | 94 | 6C | 79 | 19 | 2 | | |
| M17-41 | L63 | V82 | L90 | 97 | 3C | 93 | 4 | 3 | | |
| M17-44 | L63P | V82 | L90M | | | 93 | 5 | 2 | | |
| 98027 | L63 | V82 | L90 | 96 | 4P | 89 | 9 | 2 | 99 | 1 |
| V894713 | L63 | V82 | L90 | | | 89 | 9 | 2 | 100 | 0 |
| AR283 | L63P | V82I | L90 | | | 20 | 76 | 4 | 100 | 0 |
| AR929 | L63P | V82I/V | L90 | | | 33 | 65 | 2 | 100 | 0 |
| AR2429 | L63P | V82V/I | L90 | | | 39 | 60 | 1 | 100 | 0 |
| AP6423 | L63L/P | V82 | L90 | | | 90 | 8 | 2 | 100 | 0 |
| AP6617 | L63P | V82 | L90 | | | 89 | 10 | 1 | 100 | 0 |
| AP7010 | L63P | V82 | L90 | | | 90 | 9 | 1 | 100 | 0 |
| AP7366 | L63P | V82 | L90 | | | 90 | 8 | 2 | 100 | 0 |

The percentage of mutant in a mix is calculated as follows: % mutant = (% wild type extension + % mutant extension) × 100

TABLE 5

Evaluation of the accuracy of PSMEA and direct sequencing for detection of low Levels of variants with population based sequencing

| Method | Genotypes | | | | | | | |
|---|---|---|---|---|---|---|---|---|
| | % V82I | % V82 | % L90M | % L90 | | % V82I | % V82 | % L90M | % L90 |

| Method | % V82I | % V82 | % L90M | % L90 |
|---|---|---|---|---|
| Population based sequencing | 87.5 (28/32)* | 12.5 (4/32) | 0.0 (0/32) | 100.0 (32/32) |
| Direct DNA sequencing | 100.0 | 0.0 | 0.0 | 100.0 |
| PSMEA | 76.0 | 20.0 | 0.0 | 100.0 |

*Denotes that a total number of mutant or wild type found in 32 cloned PCR products sequenced.

What is claimed is:

1. A primer specific and mispair extension assay for determining genotype, said assay comprising:
   a) extending a nucleic acid sequence from a patient sample with pfu DNA polymerase, using a primer specific for a genotype to be determined, and an incomplete set of dNTPs in the absence of ddNTPs, under suitable conditions for obtaining one or more extension products of the primer wherein said one or more extension products are terminated in the presence of at least two mispairs within a 2 to 4 base pair range located downstream of the 3' end of the primer; and wherein at least one of the primer or the dNTPs is labeled;
   b) characterizing the extension products; and
   c) analyzing the characterized extension products based on primer-specific pairing and non-specific pairing to determine the genotype of the nucleic acid sequence extended.

2. The assay according to claim 1, wherein the step of characterizing the extension products comprises the step of separating by size said extension products.

3. The assay according to claim 1, further comprising before step a) the step of amplifying the nucleic acid sequence.

4. The assay according to claim 3, wherein the incomplete set of dNTPs contains three different types of nucleotides.

5. The assay according to claim 4, wherein the incomplete set of dNTPs contains two different types of nucleotides.

6. The assay according to claim 5, wherein the primer is labeled with a radioactive label.

7. The assay according to claim 6, wherein one of the dNTPs is labeled with a radioactive label.

8. The assay according to claim 7, wherein the primer is labeled with a fluorescent label.

9. The assay according to claim 1, wherein said extending, said characterizing and said analyzing are automated.

10. The assay according to claim 9, wherein the step of characterizing the extension products further comprises after the step of separating by size the extension products the step of sequencing the extension products.

11. The assay according to claim 2, further comprising sequencing the extension products after separating the extension products by size.

12. The assay according to claim 11, wherein said primer is selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 13, SEQ ID NO. 14 and SEQ ID NO. 15.

13. The primer specific and mispair extension assay of claim 1 wherein said at least two mispairs are created immediately following one correct pairing at the position immediately adjacent to said 3' end of the primer.

14. The primer specific and mispair extension assay of claim 1 wherein said at least two mispairs are separated by one or two correct pairings.

15. The primer specific and mispair extension assay of claim 1 wherein said at least two mispairs are consecutive mispairs.

16. A primer specific and mispair extension assay for determining genotype, said assay comprising:
   a) extending a nucleic acid sequence from a patient sample with pfu DNA polymerase, using a primer specific for a genotype to be determined, and an incomplete set of dNTPs in the absence of ddNTPs, under suitable conditions for obtaining extension products of the primer based on specific pairing and non-specific pairing, wherein said extension products are terminated in the presence of at least two mispairs within a 2 to 4 base pair range located downstream of the 3' end of the primer, and wherein at least one of the primer or dNTPs is labeled;
   b) separating the extension products obtained;
   c) characterizing the extension products;
   d) generating a genotype-specific extension profile of the extension products; and
   e) analyzing the genotype-specific extension profiles to determine a genotype of the nucleic acid sequence.

17. The assay according to claim 16, wherein said genotype is determined based on an analysis of a genotype specific primer pairing and non-specific pairing.

18. The assay according to claim 16, wherein said analysis is based on the termination of primer extension by mispair(s) and on primer specific pairing and non-specific pairing extension on a template.

* * * * *

UNITED STATES PATENT AND TRADEMARK OFFICE
CERTIFICATE OF CORRECTION

PATENT NO. : 6,811,974 B2
APPLICATION NO. : 09/782361
DATED : November 2, 2004
INVENTOR(S) : Yu-Wen Hu Page 1 of 1

It is certified that error appears in the above-identified patent and that said Letters Patent is hereby corrected as shown below:

COLUMN 1, LINES 54-55, change "(G ünthard, H. F.," to --(Günthard, H. F.,--
COLUMN 5, LINE 17, change "FIGS. 7A and 73B" to --FIGS. 7A and 7B--
COLUMN 17, LINES 43-44, change "genotype (s)" to --genotype(s)--

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 49

<210> SEQ ID NO 1
<211> LENGTH: 25
<212> TYPE: DNA
<213> ORGANISM: Artificial
<220> FEATURE:
<223> OTHER INFORMATION: sense universal primer for PCR (first round)

<400> SEQUENCE: 1

```
ctccctgtg aggaactact gtctt                                    25
```

<210> SEQ ID NO 2
<211> LENGTH: 20
<212> TYPE: DNA
<213> ORGANISM: Artificial
<220> FEATURE:
<223> OTHER INFORMATION: antisense universal primer for PCR (first
      round)

<400> SEQUENCE: 2

```
ctcgcaagca ccctatcagg                                         20
```

<210> SEQ ID NO 3
<211> LENGTH: 31
<212> TYPE: DNA
<213> ORGANISM: Artificial
<220> FEATURE:
<223> OTHER INFORMATION: sense universal primer for PCR (second round)

<400> SEQUENCE: 3

```
ccatagtggt ctgcggaacc ggtgagtaca c                            31
```

<210> SEQ ID NO 4
<211> LENGTH: 18
<212> TYPE: DNA
<213> ORGANISM: Artificial
<220> FEATURE:
<223> OTHER INFORMATION: antisense universal primer for PCR (second
      round)

<400> SEQUENCE: 4

```
cccaacacta ctcggcta                                           18
```

<210> SEQ ID NO 5
<211> LENGTH: 21
<212> TYPE: DNA
<213> ORGANISM: Artificial
<220> FEATURE:
<223> OTHER INFORMATION: primer for PSMEA

<400> SEQUENCE: 5

```
ctcaatgcct ggagatttgg g                                       21
```

<210> SEQ ID NO 6
<211> LENGTH: 20
<212> TYPE: DNA
<213> ORGANISM: Artificial
<220> FEATURE:
<223> OTHER INFORMATION: primer for PSMEA

<400> SEQUENCE: 6

```
caccggaatt gccaggacga                                         20
```

<210> SEQ ID NO 7
<211> LENGTH: 21
<212> TYPE: DNA
<213> ORGANISM: Artificial
<220> FEATURE:
<223> OTHER INFORMATION: primer for PSMEA

<400> SEQUENCE: 7

```
acactactcg gctagcagtc t                                       21
```

<210> SEQ ID NO 8
<211> LENGTH: 21

```
<212> TYPE: DNA
<213> ORGANISM: Artificial
<220> FEATURE:
<223> OTHER INFORMATION: primer for PSMEA

<400> SEQUENCE: 8
ccactctatg cccggtcatt t                                               21

<210> SEQ ID NO 9
<211> LENGTH: 21
<212> TYPE: DNA
<213> ORGANISM: Artificial
<220> FEATURE:
<223> OTHER INFORMATION: primer for PSMEA

<400> SEQUENCE: 9
tatgtccggt catttgggca c                                               21

<210> SEQ ID NO 10
<211> LENGTH: 21
<212> TYPE: DNA
<213> ORGANISM: Artificial
<220> FEATURE:
<223> OTHER INFORMATION: primer for PSMEA

<400> SEQUENCE: 10
cactctgtgc ccggccattt g                                               21

<210> SEQ ID NO 11
<211> LENGTH: 19
<212> TYPE: DNA
<213> ORGANISM: Artificial
<220> FEATURE:
<223> OTHER INFORMATION: primer for PSMEA

<400> SEQUENCE: 11
accggaatcg ctggggtga                                                  19

<210> SEQ ID NO 12
<211> LENGTH: 19
<212> TYPE: DNA
<213> ORGANISM: Artificial
<220> FEATURE:
<223> OTHER INFORMATION: primer for PSMEA

<400> SEQUENCE: 12
accggaatcg ccgggatga                                                  19

<210> SEQ ID NO 13
<211> LENGTH: 21
<212> TYPE: DNA
<213> ORGANISM: Artificial
<220> FEATURE:
<223> OTHER INFORMATION: primer for PSMEA

<400> SEQUENCE: 13
cactactcgg ctagtgatct c                                               21

<210> SEQ ID NO 14
<211> LENGTH: 19
<212> TYPE: DNA
<213> ORGANISM: Artificial
<220> FEATURE:
<223> OTHER INFORMATION: primer for PSMEA

<400> SEQUENCE: 14
```

```
gggggtcctg gaggctgtt                                                  19
```

<210> SEQ ID NO 15
<211> LENGTH: 22
<212> TYPE: DNA
<213> ORGANISM: Artificial
<220> FEATURE:
<223> OTHER INFORMATION: primer for PSMEA

<400> SEQUENCE: 15

```
cattgagcgg gtttgatcca at                                              22
```

<210> SEQ ID NO 16
<211> LENGTH: 12
<212> TYPE: DNA
<213> ORGANISM: Artificial
<220> FEATURE:
<223> OTHER INFORMATION: Extension product of wild-type HIV-1

<400> SEQUENCE: 16

```
agtccacatc ct                                                         12
```

<210> SEQ ID NO 17
<211> LENGTH: 12
<212> TYPE: DNA
<213> ORGANISM: Artificial
<220> FEATURE:
<223> OTHER INFORMATION: Extension product of wild-type HIV-1

<400> SEQUENCE: 17

```
cgtccacatc ct                                                         12
```

<210> SEQ ID NO 18
<211> LENGTH: 41
<212> TYPE: DNA
<213> ORGANISM: Artificial
<220> FEATURE:
<223> OTHER INFORMATION: L63 + primer sequences
<221> NAME/KEY: misc_feature
<222> LOCATION: (32)..(32)
<223> OTHER INFORMATION: n can be any nucleotide
<221> NAME/KEY: misc_feature
<222> LOCATION: (41)..(41)
<223> OTHER INFORMATION: n can be any nucleotide

<400> SEQUENCE: 18

```
gctttatgtc cacagatttc tatgagtacc tnatcatact n                         41
```

<210> SEQ ID NO 19
<211> LENGTH: 44
<212> TYPE: DNA
<213> ORGANISM: Artificial
<220> FEATURE:
<223> OTHER INFORMATION: L63P + primer sequences

<400> SEQUENCE: 19

```
agacagtatg atcaggtact catagaaatc tgtggacata aagc                      44
```

<210> SEQ ID NO 20
<211> LENGTH: 26
<212> TYPE: DNA
<213> ORGANISM: Artificial
<220> FEATURE:
<223> OTHER INFORMATION: pro63L(G)-R

<400> SEQUENCE: 20

```
gctttatgtc cacagatttc tatgag                                          26
```

```
<210> SEQ ID NO 21
<211> LENGTH: 44
<212> TYPE: DNA
<213> ORGANISM: Artificial
<220> FEATURE:
<223> OTHER INFORMATION: L63P + primer sequences

<400> SEQUENCE: 21
agacagtatg atcaggtacc catagaaatc tgtggacata aagc        44

<210> SEQ ID NO 22
<211> LENGTH: 41
<212> TYPE: DNA
<213> ORGANISM: Artificial
<220> FEATURE:
<223> OTHER INFORMATION: L63 + primer sequences
<221> NAME/KEY: misc_feature
<222> LOCATION: (32)..(41)
<223> OTHER INFORMATION: n can be any nucleotide

<400> SEQUENCE: 22
gctttatgtc cacagatttc tatgggtacc tnatcatact n           41

<210> SEQ ID NO 23
<211> LENGTH: 26
<212> TYPE: DNA
<213> ORGANISM: Artificial
<220> FEATURE:
<223> OTHER INFORMATION: PRO90L-R

<400> SEQUENCE: 23
gctttatgtc cacagatttc tatggg                            26

<210> SEQ ID NO 24
<211> LENGTH: 33
<212> TYPE: DNA
<213> ORGANISM: Artificial
<220> FEATURE:
<223> OTHER INFORMATION: L90
<221> NAME/KEY: misc_feature
<222> LOCATION: (32)..(33)
<223> OTHER INFORMATION: n can be any nucleotide

<400> SEQUENCE: 24
atttaaagtg caaccaatct gagtcttcag ann                    33

<210> SEQ ID NO 25
<211> LENGTH: 33
<212> TYPE: DNA
<213> ORGANISM: Artificial
<220> FEATURE:
<223> OTHER INFORMATION: L90

<400> SEQUENCE: 25
aatctgaaga ctcagattgg ttgcacttta aat                    33

<210> SEQ ID NO 26
<211> LENGTH: 27
<212> TYPE: DNA
<213> ORGANISM: Artificial
<220> FEATURE:
<223> OTHER INFORMATION: PRO90L-R

<400> SEQUENCE: 26
atttaaagtg caaccaatct gagtctt                           27
```

-continued

```
<210> SEQ ID NO 27
<211> LENGTH: 33
<212> TYPE: DNA
<213> ORGANISM: Artificial
<220> FEATURE:
<223> OTHER INFORMATION: L90M

<400> SEQUENCE: 27
aatctgatga ctcagattgg ttgcacttta aat                                    33

<210> SEQ ID NO 28
<211> LENGTH: 38
<212> TYPE: DNA
<213> ORGANISM: Artificial
<220> FEATURE:
<223> OTHER INFORMATION: PRO90M-F
<221> NAME/KEY: misc_feature
<222> LOCATION: (37)..(38)
<223> OTHER INFORMATION: n can be any nucleotide

<400> SEQUENCE: 28
ctgtcaacat aattggaaga aatctgatga cgcagann                               38

<210> SEQ ID NO 29
<211> LENGTH: 38
<212> TYPE: DNA
<213> ORGANISM: Artificial
<220> FEATURE:
<223> OTHER INFORMATION: L90M

<400> SEQUENCE: 29
aatctgcgtc atcagatttc ttccaattat gttgacag                               38

<210> SEQ ID NO 30
<211> LENGTH: 28
<212> TYPE: DNA
<213> ORGANISM: Artificial
<220> FEATURE:
<223> OTHER INFORMATION: PRO90M-F

<400> SEQUENCE: 30
ctgtcaacat aattggaaga aatctgat                                          28

<210> SEQ ID NO 31
<211> LENGTH: 38
<212> TYPE: DNA
<213> ORGANISM: Artificial
<220> FEATURE:
<223> OTHER INFORMATION: L90

<400> SEQUENCE: 31
aatctgagtc aacagatttc ttccaattat gttgacag                               38

<210> SEQ ID NO 32
<211> LENGTH: 13
<212> TYPE: DNA
<213> ORGANISM: Artificial
<220> FEATURE:
<223> OTHER INFORMATION: Extension product of a mutant HIV-1
<221> NAME/KEY: misc_feature
<222> LOCATION: (12)..(13)
<223> OTHER INFORMATION: n can be any nucleotide

<400> SEQUENCE: 32
agttgtatta ann                                                          13
```

```
<210> SEQ ID NO 33
<211> LENGTH: 18
<212> TYPE: DNA
<213> ORGANISM: Artificial
<220> FEATURE:
<223> OTHER INFORMATION: Extesion product of a wild HIV-1

<400> SEQUENCE: 33
tcaacataat tggaaaga                                                   18

<210> SEQ ID NO 34
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1a

<400> SEQUENCE: 34
tttgggcgtg cccccgcaag ac                                              22

<210> SEQ ID NO 35
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1b

<400> SEQUENCE: 35
tttgggcgtg cccccgcgag ac                                              22

<210> SEQ ID NO 36
<211> LENGTH: 18
<212> TYPE: DNA
<213> ORGANISM: Hepatitis C virus
<220> FEATURE:
<221> NAME/KEY: misc_feature
<222> LOCATION: (16)..(18)
<223> OTHER INFORMATION: N can be any nucleotide
<221> NAME/KEY: misc_feature
<223> OTHER INFORMATION: nucleotide sequence on templates for HCV
      genotype 1a

<400> SEQUENCE: 36
cgcgggggcg cgcccnnn                                                   18

<210> SEQ ID NO 37
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1a

<400> SEQUENCE: 37
gtcttgcggg ggcacgccca aa                                              22

<210> SEQ ID NO 38
<211> LENGTH: 13
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1a
```

```
<221> NAME/KEY: misc_feature
<222> LOCATION: (12)..(13)
<223> OTHER INFORMATION: n can be any nucleotide

<400> SEQUENCE: 38
cgcgcccccg cnn                                                            13

<210> SEQ ID NO 39
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1b

<400> SEQUENCE: 39
gtctcgcggg ggcacgccca aa                                                  22

<210> SEQ ID NO 40
<211> LENGTH: 15
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1b
<221> NAME/KEY: misc_feature
<222> LOCATION: (13)..(15)
<223> OTHER INFORMATION: n can be any nucleotide

<400> SEQUENCE: 40
cgcgcccccg cgnnn                                                          15

<210> SEQ ID NO 41
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1a

<400> SEQUENCE: 41
tttgggcgtg cccccgcaag ac                                                  22

<210> SEQ ID NO 42
<211> LENGTH: 18
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1a

<400> SEQUENCE: 42
cgcgggggcg cgcccaaa                                                       18

<210> SEQ ID NO 43
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1a
<221> NAME/KEY: misc_feature
<222> LOCATION: (17)..(22)
<223> OTHER INFORMATION: n can be any nucleotide
```

```
<400> SEQUENCE: 43
aggaccgggt cctttcnntt gg                                            22

<210> SEQ ID NO 44
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 6a

<400> SEQUENCE: 44
aggaccgggt cctttccatt gg                                            22

<210> SEQ ID NO 45
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 6a

<400> SEQUENCE: 45
aggaccgggt cctttccatt gg                                            22

<210> SEQ ID NO 46
<211> LENGTH: 15
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 6a
<221> NAME/KEY: misc_feature
<222> LOCATION: (15)..(15)
<223> OTHER INFORMATION: n can be any nucleotide

<400> SEQUENCE: 46
ggaaagggac ccggn                                                    15

<210> SEQ ID NO 47
<211> LENGTH: 22
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1a
<221> NAME/KEY: misc_feature
<222> LOCATION: (17)..(22)
<223> OTHER INFORMATION: n can be any nucleotide

<400> SEQUENCE: 47
aggaccgggt cctttcnntt gg                                            22

<210> SEQ ID NO 48
<211> LENGTH: 48
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 2a

<400> SEQUENCE: 48
```

```
tggccgggca tagagtgggt ttatccaaga aaggacccag tcttcccg                48
```

<210> SEQ ID NO 49
<211> LENGTH: 48
<212> TYPE: DNA
<213> ORGANISM: Hepatitis C virus
<220> FEATURE:
<221> NAME/KEY: misc_feature
<223> OTHER INFORMATION: nucleotide sequence on templates for HCV
      genotype 1b

<400> SEQUENCE: 49

```
tctccaggca ttgagcgggt tgatccaaga aaggacccgg tcgtcctg                48
```